(12) United States Patent
Najimi et al.

(10) Patent No.: US 11,793,837 B2
(45) Date of Patent: Oct. 24, 2023

(54) CONDITIONED MEDIUM FROM HUMAN ADULT LIVER STEM CELLS AND ITS USE IN THE TREATMENT OF LIVER DISORDERS

(71) Applicant: Université Catholique De Louvain, Louvain-la-Neuve (BE)

(72) Inventors: Mustapha Najimi, Brussels (BE); Etienne Sokal, Hoeilaart (BE); Silvia Berardis, Brussels (BE)

(73) Assignee: UNIVERSITÉ CATHOLIQUE DE LOUVAIN, Louvain-la-Neuve (BE)

( * ) Notice: Subject to any disclaimer, the term of this patent is extended or adjusted under 35 U.S.C. 154(b) by 236 days.

(21) Appl. No.: 17/104,202

(22) Filed: Nov. 25, 2020

(65) Prior Publication Data

US 2021/0077537 A1   Mar. 18, 2021

Related U.S. Application Data

(62) Division of application No. 15/940,897, filed on Mar. 29, 2018, now Pat. No. 10,874,699, which is a division of application No. 14/899,661, filed as application No. PCT/EP2014/064437 on Jul. 7, 2014, now abandoned.

(30) Foreign Application Priority Data

Jul. 5, 2013  (EP) .................................... 13175442

(51) Int. Cl.
| | | |
|---|---|---|
| *A61K 35/407* | (2015.01) | |
| *C12N 5/071* | (2010.01) | |
| *C12N 5/00* | (2006.01) | |

(52) U.S. Cl.
CPC .......... *A61K 35/407* (2013.01); *C12N 5/0037* (2013.01); *C12N 5/067* (2013.01); *C12N 5/0672* (2013.01); *C12N 2502/14* (2013.01)

(58) Field of Classification Search
None
See application file for complete search history.

(56) References Cited

U.S. PATENT DOCUMENTS

| | | | |
|---|---|---|---|
| 5,521,076 | A | 5/1996 | Mulligan et al. |
| 6,242,252 | B1 | 6/2001 | Reid et al. |
| 6,774,120 | B1 | 8/2004 | Ferber |
| 8,119,405 | B2 | 2/2012 | Ferber |
| 8,673,635 | B2 | 3/2014 | Sokal et al. |
| 8,778,607 | B2 | 7/2014 | Sokal et al. |
| 9,107,910 | B2 | 8/2015 | Sokal et al. |
| 9,775,863 | B2 | 10/2017 | Sokal et al. |
| 9,775,890 | B2 | 10/2017 | Stephenne et al. |
| 9,931,360 | B2 | 4/2018 | Sokal et al. |
| 2003/0078409 | A1 | 4/2003 | Holroyd et al. |
| 2003/0138951 | A1 | 7/2003 | Yin |
| 2004/0213769 | A1 | 10/2004 | Ferber |
| 2005/0074876 | A1 | 4/2005 | Strick-Marchand et al. |
| 2005/0090465 | A1 | 4/2005 | Ferber |
| 2005/0118274 | A1 | 6/2005 | Bader |
| 2011/0274664 | A1 | 11/2011 | Harn et al. |
| 2012/0329710 | A1 | 12/2012 | Ferber |
| 2013/0302291 | A1 | 11/2013 | Stephenne et al. |
| 2015/0037291 | A1 | 2/2015 | Stephenne et al. |
| 2015/0306147 | A1 | 10/2015 | Sokal et al. |
| 2016/0129047 | A1 | 5/2016 | Najimi et al. |
| 2017/0042940 | A1 | 2/2017 | Stephenne et al. |
| 2017/0354723 | A1 | 12/2017 | Stephenne et al. |

FOREIGN PATENT DOCUMENTS

| | | |
|---|---|---|
| CN | 1411504 A | 4/2003 |
| EP | 2 254 586 B1 | 4/2015 |
| JP | 2009-508650 A | 3/2009 |
| JP | 2009-520474 A | 5/2009 |
| WO | 1994/008598 A1 | 4/1994 |
| WO | 2000/072885 A2 | 12/2000 |
| WO | 2001/053462 A1 | 7/2001 |
| WO | 2001/095931 A1 | 12/2001 |
| WO | 2003/000848 A2 | 1/2003 |
| WO | 2004/098646 A1 | 11/2004 |
| WO | 2005/035738 A1 | 4/2005 |
| WO | 2006/103206 A2 | 10/2006 |

(Continued)

OTHER PUBLICATIONS

Baraniak et al, Regen Med, 2010, 5(1):121-143. (Author manuscript) (Year: 2010).*
Dohi et al, Am J Respir Crit Care Med, 2000, 162: 2302-2307. (Year: 2000).*
Zhang et al. (2005) "The existence of epithelial-to-mesenchymal cells with the ability to support hematopoiesis in human fetal liver," Cell Biology International. 29(3):213-219.
Akima et al. (2009) "Tirofiban and Activated Protein C Synergistically Inhibit the Instant Blood Mediated Inflammatory Reaction (IBMIR) from Allogeneic Islet Cells Exposure to Human Blood," American Journal of Transplantation. 9:1533-1540.

(Continued)

*Primary Examiner* — Allison M Fox

(74) *Attorney, Agent, or Firm* — LATHROP GPM LLP; James H. Velema; Judith L. Stone-Hulslander

(57) ABSTRACT

The invention relates to cell-free compositions obtained by culturing adult-derived human liver stem/progenitor cells (ADHLSC) in cell culture medium and isolating the resulting conditioned medium (ADHLSC-CM) that has advantageous properties, such as anti-fibrotic effects. ADHLSC-CM, compositions based on ADHLSC-CM, and other related and derived products, can be used in cell culture processes or as a medicament, more particularly for the treatment of diseases involving organ injury, organ failure, in organ or cell transplantation or the pathological disruption, inflammation, degeneration, and/or proliferation of cells within a tissue or an organ, in particular within liver.

14 Claims, 6 Drawing Sheets

(56) References Cited

FOREIGN PATENT DOCUMENTS

| | | |
|---|---|---|
| WO | 2006/121445 A2 | 11/2006 |
| WO | 2006/126219 A1 | 11/2006 |
| WO | 2006/126236 A1 | 11/2006 |
| WO | 2007/035843 A2 | 3/2007 |
| WO | 2007/071339 A1 | 6/2007 |
| WO | 2008/060788 A2 | 5/2008 |
| WO | 2008/070868 A1 | 6/2008 |
| WO | 2009/057165 A1 | 5/2009 |
| WO | 2009/150199 A1 | 12/2009 |
| WO | 2010/119176 A1 | 10/2010 |
| WO | 2011/010966 A1 | 1/2011 |
| WO | 2011/070001 A1 | 6/2011 |
| WO | 2012/101181 A1 | 8/2012 |
| WO | 2013/110354 A1 | 8/2013 |
| WO | 2015/001124 A1 | 1/2015 |
| WO | 2017/149059 A1 | 9/2017 |

OTHER PUBLICATIONS

Berardis et al. (Jan. 2014) "Gene Expression Profiling and Secretome Analysis Differentiate Adult-Derived Human Liver Stem/Progenitor Cells and Human Hepatic Stellate Cells," PLoS One. 9(1):e86137. pp. 1-11.

Biemond et al. (1994) "Additive Effect of the Combined Administration of Low Molecular Weight Heparin and Recombinant Hirudin on Thrombus Growth in a Rabbit Jugular Vein Thrombosis Model," Thrombosis and Haemostasis. 72(3):377-380.

Brenner et al. (2010) "Prevention of hyperacute xenograft rejection through direct thrombin inhibition with hirudin," Ann. Transplant. 15(4):30-37.

Chen et al. (2007) "Low dose heparin for the prevention of hepatic veno-occlusive disease after allogeneic hematopoietic stem cell transplantation," Chinese Journal of Internal Medicine. 46(2):140-142.—English abstract provided only.

Cuccuini et al. (2010) "Tissue factor up-regulation in proinflammatory conditions confers thrombin generation capacity to endothelial colony-forming cells without influencing non-coagulant properties in vitro," Journal of Thrombosis and Haemostasis. 8:2042-2052.

Dollet et al. (Oct. 17, 2016) "Comprehensive Screening of Cell Surface Markers Expressed by Adult-Derived Human Liver Stem/Progenitor Cells Harvested at Passage 5: Potential Implications for Engraftment," Stem Cells International. 2016:9302537. pp. 1-12.

El-Kehdy et al. (Dec. 15, 2015) "Hepatocytic Differentiation Potential of Human Fetal Liver Mesenchymal Stem Cells: In Vitro and In Vivo Evaluation," Stem Cells International. 2016:6323486. pp. 1-12.

Giardino et al. (2010) "Cooperative antithrombotic effect from the simultaneous inhibition of thrombin and factor Xa," Blood Coagulation and Fibrinolysis. 21:128-134.

Gleeson et al. (Jun. 4, 2015) "Bone Marrow-Derived Mesenchymal Stem Cells Have Innate Procoagulant Activity and Cause Microvascular Obstruction Following Intracoronary Delivery: Amelioration by Antithrombin Therapy," Stem Cells. 33:2726-2737.

Gupta et al. (1992) "Hepatocyte transplantation: development of new systems for liver repopulation and gene therapy," Semin. Liver Dis. 12(3):321-31.

International Preliminary Report on Patentability corresponding to International Patent Application No. PCT/EP2006/012046, dated Jan. 24, 2008.

International Search Report with Written Opinion corresponding to International Patent Application No. PCT/EP2012/051157, dated May 7, 2012.

International Search Report with Written Opinion corresponding to International Patent Application No. PCT/EP2012/061534, dated Oct. 1, 2012.

International Search Report with Written Opinion corresponding to International Patent Application No. PCT/EP2017/054859, dated May 12, 2017.

Linder et al. (2003) "The influence of direct and antithrombin-dependent thrombin inhibitors on the procoagulant and anticoagulant effects of thrombin," Thrombosis Research. 110:221-226.

Lisman et al. (2010) "Normal to increased thrombin generation in patients undergoing liver transplantation despite prolonged conventional coagulation tests," J. Hepatol. 52(3):355-361.

Lisman et al. (2010) "Rebalanced hemostasis in patients with liver disease: evidence and clinical consequences," Blood. 116(6):878-885.

Moll et al. (Aug. 24, 2015) "Different Procoagulant Activity of Therapeutic Mesenchymal Stromal Cells Derived from Bone Marrow and Placental Decidua," Stem Cells and Development. 24(19):2269-2279.

Pan et al. (2011) "Mobilization of hepatic mesenchymal stem cells from human liver grafts," Liver Transplantation. 17(5):596-609.

Smets et al. (2008) "Cell transplantation in the treatment of liver diseases," Pediatric Transplantation. 12:6-13.

Stephenne et al. (2012) "Bivalirudin in Combination with Heparin to Control Mesenchymal Cell Procoagulant Activity," PLoS One. 7(8):e42819. pp. 1-13.—with Supplementary Information.

Tsakiris et al. (2009) "Thrombotic complications after haematopoietic stem cell transplantation: early and late effects," Best Practice & Research Clinical Haematology. 22:137-145.

Welsby et al. (2007) "Effect of Combined Anticoagulation Using Heparin and Bivalirudin on the Hemostatic and Inflammatory Responses to Cardiopulmonary Bypass in the Rat," Anesthesiology. 106(2):295-301.

Atoui et al. (Mar. 12, 2012) "Concise Review: Immunomodulatory Properties of Mesenchymal Stem Cells in Cellular Transplantation: Update, Controversies, and Unknowns," Stem Cells Trans!. Med. 1(3):200-205.

Avigdor et al. (2004) "CD44 and Hyaluronic Acid Cooperate with SDF-1 in the Trafficking of Human CD34+ Stem/Progenitor Cells to Bone Marrow," Blood. 103(8):2981-2989.

Avital et al. (2002) "Bone Marrow-derived Liver Stem Cell and Mature Hepatocyte Engraftment in Livers Undergoing Rejection," Surgery. 132(2):384-390.

Azuma et al. (2003) "Enrichment of Hepatic Progenitor Cells from Adult Mouse Liver," Hepatology. 37(6):1385-1394.

Baglio et al. (Jun. 13, 2012) "Mesenchymal stem cell secreted vesicles provide novel opportunities in (stem) cell-free therapy," Front Physiol. 3:359. pp. 1-11.

Barry et al. (2001) "The SH-3 and SH-4 Antibodies Recognize Distinct Epitopes on CD73 from Human Mesenchymal Stem Cells," Biochemical and Biophysical Research Communications. 289(2):519-524.

Bartholomew et al. (2001) "Baboon Mesenchymal Stem Cells can be Genetically Modified to Secrete Human Erythropoietin In Vivo," Human Gene Therapy. 12(12):1527-1541.

Boiret et al. (2005) "Characterization of Nonexpanded Mesenchymal Progenitor Cells from Normal Adult Human Bone Marrow," Experimental Hematology. 33(2):219-225.

Cavallari et al. (Apr. 2, 2012) "Role of Lefty in the anti tumor activity of human adult liver stem cells," Oncogene. 32:819-826.

Chagraoui et al. (2003) "Fetal Liver Stroma Consists of Cells in Epithelial-to-Mesenchymal Transition," Blood. 101 (8):2973-2982.

Chen et al. (2007) "In Vitro Differentiation of Mouse Bone Marrow Stromal Stem Cells Into Hepatocytes Induced by Conditioned Culture Medium of Hepatocytes," Journal of Cellular Biochemistry. 102:52-63.

Covas et al. (2005) "Mesenchymal Stem Cells can be Obtained from the Human Saphena Vein," Experimental Cell Research. 309(2):240-244.

Dabeva et al. (1997) "Differentiation of Pancreatic Epithelial Progenitor Cells into Hepatocytes Following Transplantation into Rat Liver," Proc. Natl. Acad. Sci. USA. 94(14):7356-7361.

Dhawan et al. (2006) "Hepatocyte Transplantation for Liver-based Metabolic Disorders," Journal of Inherited Metabolic Disease. 29:431-435.

Di Campli et al. (2004) "A Human Umbilical Cord Stem Cell Rescue Therapy in a Murine Model of Toxic Liver Injury," Digestive and Liver Disease. 36(9):603-613.

(56) References Cited

OTHER PUBLICATIONS

Dimitroff et al. (2001) "CD44 is a Major E-Selectin Ligand on Human Hematopoietic Progenitor Cells," Journal of Cell Biology. 153(6):1277-1286.
Dragoo et al. (2003) "Bone Induction by BMP-2 Transduced Stem Cells Derived from Human Fat," Journal of Orthopaedic Research. 21(4):622-629.
Du et al. (Mar. 6, 2013) "Mesenchymal stem cell-conditioned medium reduces liver injury and enhances regeneration in reduced-size rat liver transplantation," J. Surg. Res. 183:907-915.
Eichelbaum et al. (Sep. 23, 2012) "Selective enrichment of newly synthesized proteins for quantitative secretome analysis," Nat. Biotechnol. 30:984-990.
Ellor et al. (2008) "Stem Cell Therapy For Inherited Metabolic Disorders Of The Liver," Exp. Hematol. 36 (6):716-725.
Espinosa-Heidmann et al. (2003) "Bone Marrow-derived Progenitor Cells Contribute to Experimental Choroidal Neovascularizaton," Investigative Ophthalmology & Visual Science. 44(11):4914-4919.
Fang et al. (2004) "Systemic Infusion of FLK1+ Meschenchymal Stem Cells Ameliorate Carbon Tetrachloride induced Liver Fibrosis in Mice," Transplantation. 78(1):83-88.
Ferber et al. (2000) "Pancreatic and duodenal homeobox gene 1 induces expression of insulin genes in liver and ameliorates streptozotocin-induced hyperglycemia," Nature Medicine. 6(5):568-572.
Furnus et al. (2003) "The Hyaluronic Acid Receptor (CD44) is Expressed in Bovine Oocytes and Early Stage Embryos," Theriogenology. 60(9):1633-1644.
Guimaraes et al. (2010) "Advanced glycation end products induce production of reactive oxygen species via the activation of NADPH oxidase in murine hepatic stellate cells," J. Hepatol. 52:389-397.
Haleem-Smith et al. (2005) "Optimization of High-efficiency Transfection of Adult Human Mesenchymal Stem Cells in Vitro," Molecular Biotechnology. 30(1):9-20.
Herrera et al. (2006) "Isolation and Characterization of a Stem Cell Population from Adult Human Liver," Stem Cells. 24(12):2840-2850.
Herrera et al. (2010) "Human liver stem cell-derived microvesicles accelerate hepatic regeneration in hepatectomized rats," Journal of Cellular and Molecular Medicine. 14(6B):1605-1618.
Herrera et al. (Jan. 7, 2013) "Human liver stem cells improve liver injury in a model of fulminant liver failure," Hepatology. 57(1):311-319.—with Supplementary Information.
Hisatomi et al. (2004) "Flow Cytometric Isolation of Endodermal Progenitors from Mouse Salivary Gland Differentiate into Hepatic and Pancreatic Lineages," Hepatology. 39(3):667-675.
Hoppo et al. (2004) "Thy1-positive Mesenchymal Cells Promote the Maturation of CD49f-positive Hepatic Progenitor Cells in the Mouse Fetal Liver," Hepatology. 39(5): 1362-1370.
Igura et al. (2004) "Isolation and Characterization of Mesenchymal Progenitor Cells from Chorionic Villi of Human Placenta," Cytotherapy. 6(6):543-553.
International Preliminary Report on Patentability corresponding to International Patent Application No. PCT/EP2014/064437, dated Jan. 5, 2016.
International Search Report with Written Opinion corresponding to International Patent Application No. PCT/EP2006/012046, dated May 4, 2007.
International Search Report with Written Opinion corresponding to International Patent Application No. PCT/EP2014/064437, dated Dec. 16, 2014.
Jostarndt-Fogen et al. (1998) "Expression of Smooth Muscle Markers in the Developing Murine Lung: Potential Contractile Properties and Lineal Descent," Histochemistry and Cellular Biology, vol. 110(3):273-284.
Keating (Jun. 14, 2012) "Mesenchymal stromal cells: new directions," Cell Stem Cell. 10:709-716.
Khuu et al. (2011) "In vitro differentiated adult human liver progenitor cells display mature hepatic metabolic functions: a potential tool for in vitro pharmacotoxicological testing," Cell Transplant. 20(2):287-302.
Khuu et al. (Dec. 4, 2012) "Adult Human Liver Mesenchymal Stem/Progenitor Cells Participate in Mouse Liver Regeneration After Hepatectomy," Cell Transplant. 22(8):1369-1380.
Kicic et al. (2005) "Are Stem Cell Characteristics Altered by Disease State?" Stem Cells and Development. 14 (1):15-28.
Kim et al. (1995) "Functional Human Hepatocytes: Isolation from Small Liver Biopsy Samples and Primary Cultivation with Liver-specific Functions," The Journal of Toxicological Sciences. 20(5):565-578.
Kim et al. (2009) "Formation of Vitamin A Lipid Droplets in Pancreatic Stellate Cells Requires Albumin," Gut. 58:1382-1390.
Ko et al. (2004) "Expression of the Intermediate Filament Vimentin in Proliferating Duct Cells as a Marker of Pancreatic Precursor Cells," Pancreas. 28(2):121-128.
Kordes et al. (2007) "CD133+ hepatic stellate cells are progenitor cells," Biochem. Biophys. Res. Common. 352:410-417.
Kordes et al. (Feb. 28, 2013) "Hepatic stellate cells support hematopoiesis and are liver-resident mesenchymal stem cells," Cell Physiol. Biochem. 31:290-304.
Kwon et al. (2005) "Cellular Manipulation of Human Embryonic Stem Cells by TAT-PDX1 Protein Transduction," Molecular Therapy. 12(1):28-32.
Lange et al. (2005) "Liver-specific Gene Expression in Mesenchymal Stem Cells is Induced by Liver Cells," World Journal of Gastroenterology. 11(29):4497-4504.
Laurson et al. (2005) "Hepatocyte Progenitors in Man and in Rodents—Multiple Pathways, Multiple Candidates," International Journal of Experimental Pathology. 86(1):1-18.
Lavoie et al. (Dec. 2013) "Uncovering the secretes of mesenchymal stem cells," Biochimie. 95(12):2212-2221.
Lazaro et al. (1998) "Generation of Hepatocytes from Oval Cell Precursors in Culture," Cancer Research. 58 (23):5514-5522.
Lee et al. (2001) "Human Mesenchymal Stem Cells Maintain Transgene Expression during Expansion and Differentiation," Molecular Therapy. 3(6):857-866.
Lee et al. (2004) "Mesenchymal Stem Cells from Cryopreserved Human Umbilical Cord Blood," Biochemical and Biophysical Research Communications. 320(1):273-278.
Lehmann et al. (1987) "Lethal toxicity of lipopolysaccharide and tumor necrosis factor in normal and D-galactosamine-treated mice," J. Exp. Med. 165:657-663.
Li et al. (2010) "Human mesenchymal stem cells inhibit metastasis of a hepatocellular carcinoma model using the MHCC97-H cell line," Cancer Science. 101:2546-2553.
Lim et al. (2002) "Modulation of Cytokeratin Expression During In vitro Cultivation of Human Hepatic Stellate Cells Evidence of Transdifferentiation from Epithelial to Mesenchymal Phenotype," Histochemistry and Cell Biology. 118 (2):127-136.
Ma et al. (2005) "Advances in isolation and culture technology of liver stem cells," Biomedical Engineering and Clinical Medicine. 9(3):175-178.—English machine translation of the abstract.
Marx et al. (1999) "High-efficiency Transduction and Long-term Gene Expression with a Murine Stem Cell Retroviral Vector Encoding the Green Fluorescent Protein in Human Marrow Stromal Cells," Human Gene Therapy. 10 (7):1163-1173.
McGuckin et al. (2005) "Production of Stem Cells with Embryonic Characteristics from Human Umbilical Cord Blood," Cell Proliferation. 38(4):245-255.
Meivar-Levy et al. (2003) "New organs from our own tissues: liver-to-pancreas transdifferentiation," Trends in Endocrinology and Metabolism. 14(10):460-466.
Meivar-Levy et al. (2006) "Regenerative Medicine: Using Liver to Generate Pancreas for Treating Diabetes," IMAJ. 8(6):430-434.
Milbrandt et al. (2003) "Tracing Transduced Cells in Osteochondral Defects," Journal of Pediatric Orthopaedics. 23 (4):430-436.
Mukherjee et al. (Jan. 31, 2013) "Methodologies to decipher the cell secretome," Biochim. Biophys. Acta. 1834:2226-2232.

(56) References Cited

OTHER PUBLICATIONS

Najimi et al. (2007) "Adult-derived human liver mesenchymal-like cells as a potential progenitor reservoir of hepatocytes?" Cell Transplant. 16:717-728.
Naughton et al. (1995) "A Stereotypic, Transplantable Liver Tissue-Culture System," Applied Biochemistry and Biotechnology. 54:65-91.
Nava et al. (2005) "Characterization of Cells in the Developing Human Liver," Differentiation. 73(5):249-260.
Oshima et al. (2005) "Behavior of Transplanted Bone Marrow-derived GFP Mesenchymal Cells in Osteochondral Defect as a Simulation of Autologous Transplantation," Journal of Histochemistry & Cytochemistry. 53(2):207-216.
Pan et al. (May 18, 2012) "Bone marrow mesenchymal stem cells ameliorate hepatic ischemia/reperfusion injuries via inactivation of the MEK/ERK signaling pathway in rats," J. Surg. Res. 178:935-948.
Panepucci et al. (2004) "Comparison of Gene Expression of Umbilical Cord Vein and Bone Marrow-derived Mesenchymal Stem Cells," Stem Cells. 22(7):1263-1278.
Parekkadan et al. (2007) "Mesenchymal stem cell-derived molecules reverse fulminant hepatic failure," PLoS ONE. 26:e941. pp. 1-6.
Piscaglia et al. (2010) "Stem Cell-based Therapies for Liver Diseases: State of the Art and New Perspectives," Stem Cells International. 2010:259461, 10 pgs.
Puglisi et al. (2011) "Therapeutic implications of mesenchymal stem cells in liver injury," J. Blamed. Biotechnol. 2011:860578. pp. 1-8.
Qiao et al. (2008) "Suppression of tumorigenesis by human mesenchymal stem cells in a hepatoma model," Cell Research. 18:500-507.
Ren et al. (Dec. 7, 2011) "Concise review: mesenchymal stem cells and translational medicine: emerging issues," Stem Cells Trans. Med. 1:51-58.
Sabatini et al. (2005) "Human Bronchial Fibroblasts Exhibit a Mesenchymal Stem Cell Phenotype and Multilineage Differentiating Potentialities," Laboratory Investigation. 85(8):962-971.
Sapir et al. (2005) "Cell-replacement therapy for diabetes: Generating functional insulin-producing tissue from adult human liver cells," Proc Natl Arad Sci. 102(22):7964-7969.
Sarugaser et al. (2005) "Human Umbilical Cord Perivascular (HUCPV) Cells: A Source of Mesenchymal progenitors," Stem Cells. 23(2):220-229.
Schwartz et al. (2002) "Multipotent Adult Progenitor Cells from Bone Marrow Differentiate into Functional Hepatocyte-like Cells," The Journal of Clinical Investigation. 109(10):1291-1302.
Shi et al. (2003) "Perivascular Niche of Postnatal Mesenchymal Stem Cells in Human Bone Marrow and Dental Pulp," Journal of Bone and Mineral Research. 18(4):696-704.
Shiojiri et al. (1991) "Cell Lineages and Oval Cell Progenitors in Rat Liver Development," Cancer Research. 51 (10):2611-2620.
Shipp et al. (1983) "Hematopoietic Differentiation Antigens That are Membrane-associated Enzymes: Cutting is the Key!," Blood. 82(4):1052-1070.
Song et al. (2004) "Ex Vivo transduced liver progenitor cells as a platform for gene therapy in mice," Hepatol. 40 (4):918-924.
Stutchfield et al. (2010) "Prospects for Stem Cell Transplantation in the Treatment of Hepatic Disease," Liver Transplantation. 16(7):827-836.
Tamayo (1983) "Is cirrhosis of the liver experimentally produced by CCl4 and adequate model of human cirrhosis?" Hepatology. 3(1):112-120.
Tateno et al. (1996) "Growth and Differentiation in Culture of Clonogenic Hepatocytes that Express Both Phenotypes of Hepatocytes and Biliary Epithelial Cells," American Journal of Pathology. 149(5):1593-1605.
Totsugawa et al. (2002) "Lentiviral Transfer of the LacZ Gene into Human Endothelial Cells and Human Bone Marrow Mesenchymal Stem Cells," Cell Transplantation. 11(5):481-488.
Turner et al. (2007) Human Hepatoblast Phenotype Maintained by Hyaluronan Hydrogels, Journal of Biomedical Materials Research Part B: Applied Biomaterials. 82(1):156-168, Abstract only.
Ueno et al. (Mar. 13, 2013) "Mesenchymal stem cells ameliorate experimental peritoneal fibrosis by suppressing inflammation and inhibiting TGF-61 signaling," Kidney Int. 84(2):297-307.
Van Poll et al. (2008) "Mesenchymal stem cell-derived molecules directly modulate hepatocellular death and regeneration in vitro and in vivo," Hepatology. 47:1634-1643.
Walkup et al. (2006) "Hepatic Stem Cells: In Search Of," Stem Cells. 24(8):1833-18409.
Wang et al. (2003) "Proliferation and Hepatic Differentiation of Adult-Derived Progenitor Cells," Cells, Tissues, Organs. 173(4):193-203.
Wang et al. (2004) "Expression of Hepatocyte-like Phenotypes in Bone Marrow Stromal Cells after HGF Induction," Biochemical and Biophysical Research Communications. 320(3):712-716.
Wang et al. (2004) "Mesenchymal Stem Cells in the Wharton's Jelly of the Human Umbilical Cord," Stem Cells. 22 (7):1330-1337.
Wang et al. (Apr. 30, 2012) "Clinical applications of mesenchymal stem cells," J. Hematol. Oncol. 5:19.
Weber et al. (2004) "Immortalization of hepatic progenitor cells," Pathologie Biologie. 52:93-96.
Wu et al. (Aug. 15, 2012) "Hepatocyte differentiation of mesenchymal stem cells," Hepatobiliary Pancreat. Dis. Int. 11:360-371.
Xagorari et al. (Apr. 15, 2013) "Protective effect of mesenchymal stem cell-conditioned medium on hepatic cell apoptosis after acute liver injury," Int. J. Clin. Exp. Pathol. 6:831-840.
Xiao et al. (2013) "Secretome of Mesenchymal Stem Cells," In; Essentials of Mesenchymal Stem Cell Biology and Its Clinical Translation. Ed.: Zhao. Springer, pp. 33-46.
Yagi et al. (2009) "Long-term superior performance of a stem cell/hepatocyte device for the treatment of acute liver failure," Tissue Eng. Part A. 15:3377-3388.
Yamamoto et al. (2004) "A Subpopulation of Bone Marrow Cells Depleted by a Novel Antibody, Anti-Liv8, is Useful for Cell Therapy to Repair Damaged Liver," Biochemical and Biophysical Research Communications. 313 (4):1110-1118.
Zarrinpar et al. (Jun. 11, 2013) "Liver transplantation: past, present and future," Nature Reviews Gastroenterology and Hepatology. 10:434-440.

* cited by examiner

Fig. 5A
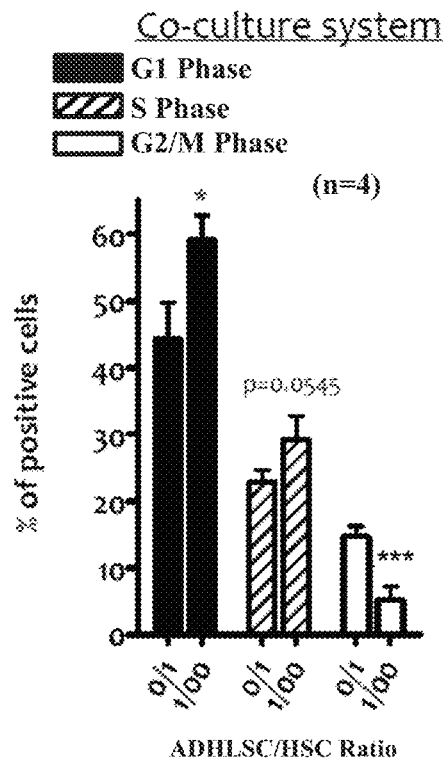
Fig. 5B
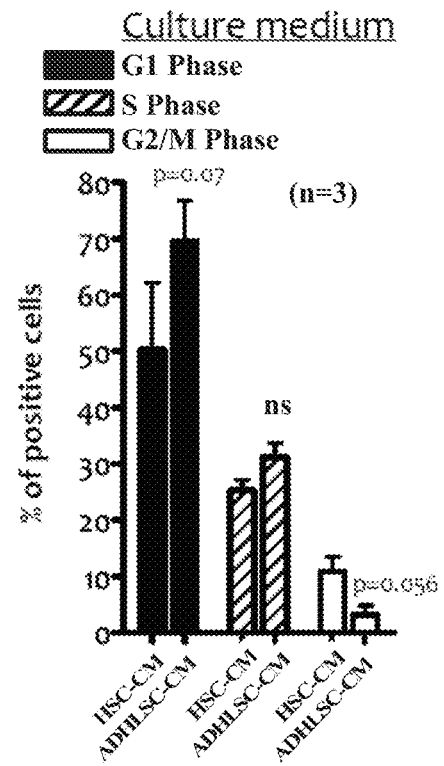
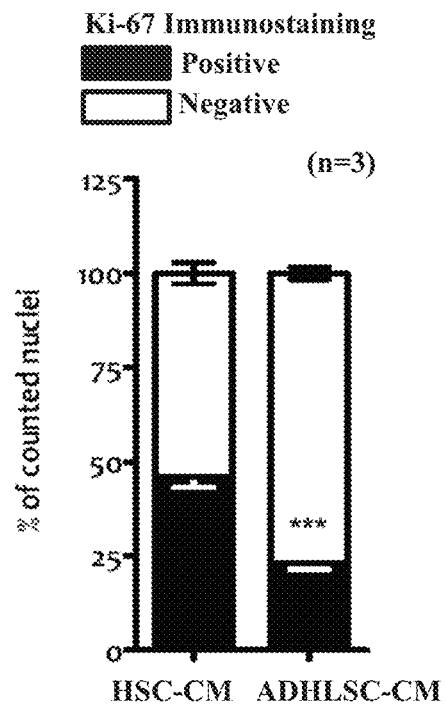
Fig. 5C

CONDITIONED MEDIUM FROM HUMAN ADULT LIVER STEM CELLS AND ITS USE IN THE TREATMENT OF LIVER DISORDERS

CROSS REFERENCE TO RELATED APPLICATIONS

This application is a divisional of U.S. patent application Ser. No. 15/940,897, filed Mar. 29, 2018, which is a divisional of U.S. patent application Ser. No. 14/899,661, filed Dec. 18, 2015, which is a 35 U.S.C. § 371 filing of International Application No. PCT/EP2014/064437, filed Jul. 7, 2014, which claims priority to European Patent Application No. 13175442.6, filed Jul. 5, 2013, each of which are incorporated herein by reference in their entireties.

FIELD

The invention broadly pertains to medical, (bio-)pharmaceutical and pharmacological fields, and particularly concerns products, including substances, compositions, and kits of parts, as well as methods and uses useful in treating diseases and disorders, such as but without limitation diseases and disorders affecting the liver.

BACKGROUND

Various conditions caused by diseased or otherwise damaged or functionally impaired organs may be treated by organ transplantation. In particular, transplantation of heart, kidneys, liver, lungs, pancreas, intestine, and thymus can routinely be performed with a reasonable rate of success. Some major drawbacks in organ transplantation, however, still remain, in particular organ shortage, the need to find a compatible donor for each recipient patient to minimise rejection of the transplanted organ, and the need for life-long immunosuppression, as summarized in connection to liver transplantation (Zarrinpar A and Busuttil R, 2013).

In recent years, therapies based on the administration of various cell types have been increasingly developed for regenerative medicine in humans. Cell transplantation may provide a valuable alternative, temporary, or additional (adjunctive) therapy to organ transplantation. Mesenchymal stromal/stem cells (MSC) represent a much investigated cell type for clinical applications, such as cell-based therapies for regenerative medicine, due to the relative ease with which such cells can be harvested from various tissues and expanded in vitro for a better characterization regarding their marker profile, self-renewal properties, and differentiation capacity (Ren G et al., 2012; Wang S et al., 2012).

Besides serving as a source of cells for replacing lost or inactive endogenous cells, MSC also exert positive effects on tissues and organs by secreting molecules (including cytokines, extracellular matrix proteins, chemokines, growth factors, and enzymes) as soluble entities or microvesicles. Such mechanisms of action are behind the attribution of a variety of paracrine MSC effects on endogenous cells of major importance for establishing MSC-based therapies, such as immunomodulation, tissue remodelling, cell migration, proliferation and survival (Atoui R and Chiu R C, 2012; Keating A. 2012; Baglio S et al., 2012).

This evidence suggests that proteins secreted by MSC (the so-called MSC secretome) may be not only contributing to the mechanisms by which MSC exert their effects but also directly exerting some of such effects alone, as a cell-free composition. Thus, MSC secretome has been studied in various systems and with different techniques, showing how its composition and activity depend on cell origin as well as on cell culture parameters (Xiao Y et al, 2013; Lavoie J and Rosu-Myles M, 2013).

MSC secretomes that have been obtained by using cells of different origins revealed distinct compositions and have been described in association to various therapeutic or in vitro uses, and to different administration approaches (WO 2008060788; WO 2008070868; WO 2011010966; WO 2010119176; WO 2006121445).

Relevant data have been also obtained in vivo, for example by showing that i) the administration of intravenous bolus of conditioned medium of bone marrow-derived MSC improves survival in a rat model of fulminant hepatic failure (Parekkadan B et al. 2007) and ii) the infusion of MSC conditioned media provides a significant survival benefit in a D-galactosamine-induced rat model of acute liver injury, preventing the release of liver injury biomarkers (van Poll D et al., 2008). MSC conditioned media have a protective effect on hepatic cell apoptosis after acute liver injury (Xagorari A et al., 2013), in reduced-size rat liver transplantation (Du Z et al., 2013) and in a rat model of hepatic ischemia/reperfusion injuries (Pan G et al., 2012). Besides their involvement in liver regeneration and liver function recovery (WO 2009057165; EP2254586; WO 2009150199), specific components of MSC secretome can be identified as providing anti-tumour activity (Cavallari C et al., 2013).

Taken together, cell/tissue regenerative therapies are clearly gaining prominence in modern medicine. However, cell-based therapies have some drawbacks. For instance, cells may cause immune reactions when administered, requiring immuno-suppression; there exists some, even if very limited, risk that stem cells may proliferate uncontrollably when administered, leading to tumours or cancers, or that they may differentiate inappropriately in vivo; cells may lose viability and thus therapeutic efficacy if not handled carefully; etc. MSC conditioned media may provide some improvement, but there persists a need to identify further and potentially improved compositions useful in cell/tissue regenerative therapy, and possibly in other indications.

SUMMARY

As illustrated for representative non-limiting embodiments of the invention in the experimental section, a cell-free composition obtained by culturing adult-derived human liver stem/progenitor cells (ADHLSC; WO2007/071339; Najimi M et al., 2007; Khuu D et al., 2012) in cell culture medium and isolating the resulting conditioned medium (ADHLSC-CM) has unexpectedly advantageous components and properties, such as anti-fibrotic effects. ADHLSC-CM, compositions based on ADHLSC-CM, and other related and derived products, can be used in cell culture processes or as a medicament, more particularly for the treatment of diseases involving organ injury, organ failure, in organ or cell transplantation, or the pathological disruption, inflammation, degeneration, and/or proliferation of cells within a tissue or an organ, in particular within liver.

Such cell-free compositions comprise, or are derived from, cell culture media that have been conditioned by culturing ADHLSC, in particular those co-expressing at least one mesenchymal marker selected from (selected from the group consisting of) CD90, CD73, CD44, vimentin and α-smooth muscle actin with at least a hepatic marker selected from (selected from the group consisting of) albumin, CD29, alpha-fetoprotein, alpha-1 antitrypsin, HNF-4 and MRP2 transporter. Still preferably ADHLSC are characterized as being albumin-positive, vimentin-positive, alpha smooth muscle actin-positive, cytokeratin-19-negative, and CD133-negative.

Conditioned medium of ADHLSC comprises useful amounts of a plurality of specific biological molecules, including among others growth factors, chemokines, matrix metalloproteases, and pro- and anti-inflammatory cytokines whose combination within ADHLSC-CM can be provide useful biological activities. The advantageous composition and properties of ADHLSC conditioned medium clearly renders this conditioned medium qualitatively and functionally different from other conditioned media, in particular those obtained from hepatic stellate cells and mesenchymal stem cells (MSC). Consequently, ADHLSC-CM or fractions thereof provide novel products and methods that are useful in a wide variety of applications, in particular for treating diseases. In view of the liver origin of ADHLSC and proven benefit of transplantation of ADHLSC into injured liver, such diseases may in particular but without limitation include diseases affecting liver.

Accordingly, an aspect of the invention provides a cell-free conditioned medium obtainable by culturing adult-derived human liver stem/progenitor cells (ADHLSC) in a cell culture medium and separating the cell culture medium from the cells. This cell-free conditioned medium of ADHLSC may also be denoted herein as "medium conditioned by ADHLSC", or simply ADHLSC-CM. The medium may in certain preferred embodiments be obtained by using serum-free medium.

A further aspect of the invention provides a product derived from ADHLSC-CM, which is a cell-free composition that is obtainable by fractioning ADHLSC-CM. Such fractioning may comprise applying one or more technologies known in the art, such as for example filtering, enzymatically digesting, centrifuging, adsorbing, and/or separating by chromatography, to ADHLSC-CM.

The ADHLSC-CM, as well as the cell-free compositions that are obtained by fractioning ADHLSC-CM, will typically contain soluble proteins and/or microvesicles. If ADHLSC-CM will potentially contain both these types of components, depending on the technology that may be applied for obtaining or fractioning the cell-free compositions as taught herein, this can provide an enrichment (or a selection) for both of them or for only of one of these types of components.

In certain embodiments, the ADHLSC-CM, as well as the cell-free compositions that are obtained by fractioning ADHLSC-CM, contains soluble proteins comprising:
(a) at least one of soluble proteins selected from the group consisting of: hepatocyte growth factor (HGF), vascular endothelial growth factor (VEGF), eotaxin (CCL11), interleukin-6 (IL-6), and interleukin-8 (IL-8); and, optionally
(b) at least one of soluble proteins selected from the group consisting of matrix metalloproteases, growth factors, chemokines, and cytokines.

Such soluble proteins may be preferably present in the ADHLSC-CM, or in the cell-free compositions that are obtained by fractioning ADHLSC-CM, at a concentration of at least 1 ng/ml. In particular, one or more of HGF, VEGF, CCL11, IL-6, or IL-8 (preferably all of them) may be present at a concentration of at least 1 ng/ml.

In certain further embodiments, the ADHLSC-CM, as well as the cell-free compositions that are obtained by fractioning ADHLSC-CM, contains microvesicles that are characterized and, when appropriate, selected according to their size (in certain embodiments, size smaller than 0.40 µm), molecular weight, and/or composition.

Particularly desired concentrations of such soluble proteins and/or microvesicles within ADHLSC-CM, or within the cell-free compositions that are obtained by fractioning ADHLSC-CM, can be obtained for example by appropriately concentrating (or diluting) the respective preparation at least about 5-fold, at least about 10-fold, at least about 20-fold, at least about 50-fold, or at least about 100-fold. Hence, certain embodiments provide so-concentrated or so-diluted ADHLSC-CM, as well as the cell-free compositions that are obtained by fractioning ADHLSC-CM.

In a further embodiment, the present invention provides a method for producing a cell-free conditioned medium comprising the steps of culturing ADHLSC in a cell culture medium and separating the cell culture medium from ADHLSC. In certain embodiments, the method may be performed by using a cell culture medium that is a serum-free medium, by modifying specific conditions of cell culture, and/or by separating the cell culture medium from ADHLSC after culturing ADHLSC in the cell culture medium for at least 2 hours, at least 4 hours, at least 6 hours, at least 8 hours, at least 12 hours, or at least 24 hours. Such ADHLSC preferably co-express at least one mesenchymal marker selected from CD90, CD73, CD44, vimentin and α-smooth muscle actin with at least an hepatic marker selected from albumin, CD29, alpha-fetoprotein, alpha-1 antitrypsin, HNF-4 and MRP2 transporter.

In a further embodiment, the present invention provides a method for producing a cell-free composition comprising hepatocyte growth factor (HGF), vascular endothelial growth factor (VEGF), eotaxin (CCL11), interleukin-6 (IL-6), and interleukin-8 (IL-8) at a concentration of at least 1 ng/ml comprising the steps of culturing adult-derived human liver stem/progenitor cells (ADHLSC) in a cell culture medium and separating the cell culture medium from the cells.

The ADHLSC-CM and cell-free compositions that are obtained by fractioning ADHLSC-CM, as intended herein, can be suitable for various applications. Such applications may generally encompass exposing cells, such as preferably but without limitation, cells of liver origin, in vitro, ex vivo, or in vivo, to the ADHLSC-CM or the cell-free compositions that are obtained by fractioning ADHLSC-CM.

Hence, in an aspect the invention provides the ADHLSC-CM or the cell-free compositions that are obtained by fractioning ADHLSC-CM, for use as a medicament.

Such medical, e.g., prophylactic or therapeutic, uses may involve using ADHLSC-CM or the cell-free compositions that are obtained by fractioning ADHLSC-CM alone or in combination with one or more exogenous active ingredients, which may be suitably added. Examples of such exogenous active ingredients include cells (e.g., ADHLSC or other cells suitable for ex vivo or in vivo applications), proteins (e.g., matrix metalloproteases, growth factors, chemokines, cytokines, hormones, antigens, or antibodies), nutrients (e.g., sugars or vitamins) and/or chemicals (e.g., drugs with immunomodulating, anti-fibrotic, or antiviral properties) that were not initially present in ADHLSC-CM or in the cell-free compositions, and that are known to be effective as medicaments for the desired indication.

In a further embodiment, the present invention provides pharmaceutical formulations comprising a pharmaceutically effective amount of ADHLSC-CM or of the cell-free compositions that are obtained by fractioning ADHLSC-CM. The pharmaceutical formulations may optionally also further comprise a pharmaceutically effective amount of one or more exogenous active ingredients, which may be of the type discussed above, e.g., the cells, proteins, nutrients, and/or chemicals.

Another embodiment thus provides a pharmaceutical formulation comprising a pharmaceutically effective amount of a combination of the ADHLSC-CM or of the cell-free compositions that are obtained by fractioning ADHLSC-CM, and one or more exogenous active ingredients. The exogenous active ingredients may be of the type discussed above, e.g., the cells, proteins, nutrients, and/or chemicals.

In a further embodiment, the present invention provides ADHLSC-CM or the cell-free compositions that are obtained by fractioning ADHLSC-CM, or the pharmaceutical formulation as defined herein, for use in the treatment (as a prophylaxis or a therapy) of a series of disorders such as fibrotic disorders, liver disorders, organ injury or failure, or any other or the pathological disruption, inflammation, degeneration, and/or proliferation within an organ or a tissue. Hence, also provided is use of ADHLSC-CM or the cell-free compositions that are obtained by fractioning ADHLSC-CM, or the pharmaceutical formulation as defined herein, for the preparation of a medicament to treat a series of disorders such as fibrotic disorders, liver disorders, organ injury or failure, or any other or the pathological disruption, inflammation, degeneration, and/or proliferation within an organ or a tissue.

Moreover, ADHLSC-CM or the cell-free compositions that are obtained by fractioning ADHLSC-CM, or the pharmaceutical formulation as defined herein, or a combination of two or more thereof, can be used in organ or cell transplantation, in a preferred example, as a subsidiary treatment that can be administered before, after, or when performing transplantation. Also provided is thus the use of ADHLSC-CM or the cell-free compositions that are obtained by fractioning ADHLSC-CM, or the pharmaceutical formulation as defined herein, or a combination of two or more thereof, for the preparation of a medicament for organ or cell transplantation, in a preferred example, as a subsidiary treatment that can be administered before, after, or when performing transplantation.

In a further aspect, the present invention provides a method of treating a disorder (such as in particular a fibrotic disorder, liver disorder, or organ injury or failure) in a subject in need of said treatment comprising the administration of a therapeutically or prophylactically effective amount of ADHLSC-CM, or the cell-free composition that is obtainable by fractioning ADHLSC-CM, or the pharmaceutical formulation as defined above, to the subject, applying the appropriate method and frequency of administration.

These and further aspects and preferred embodiments of the invention are described in the following sections and in the appended claims. The subject-matter of the appended claims is hereby specifically incorporated in this specification.

BRIEF DESCRIPTION OF DRAWINGS

FIGS. 5A-5C: effects of ADHLSC and ADHLSC-CM on HSC cell cycle and proliferation. The effect is assessed by Propidium Iodide staining (FIGS. 5A-5B) and by Ki-67 immunostaining (FIG. 5C), showing the quantitative effect of exposing HSC to ADHLSC in the Transwell® co-culture system (FIG. 5A) or by adding directly ADHLSC-CM (FIGS. 5B-5C) on the percentage of HSC in a given state. The Ki67 immunostaining of HSC showed a significant decrease of the number of immunostained nuclei of HSC pre-incubated for 24 hours with ADHLSC-CM. Similarly to the effect on floating or adherent HSC (see FIG. 3), at lower ADHLSC/HSC ratios (1/1000 and 1/10000), the effect on the number of HSC that are in either G0/G1 Phase or G2/M phase is not statistically significant, confirming that 1/100 ratio, as shown in the Figure, is a particularly effective experimental condition for evaluating the effect of ADHLSC secretome. For the analysis of statistically relevant differences between the different conditions or between ADHLSC-CM and HSC-CM, *** denotes a p value <0.001 and * denotes a p value <0.05; other relevantp values are indicated. ns: not significant. n: number of donors for which the experiment was performed.

DESCRIPTION OF EMBODIMENTS

Figure 1A:
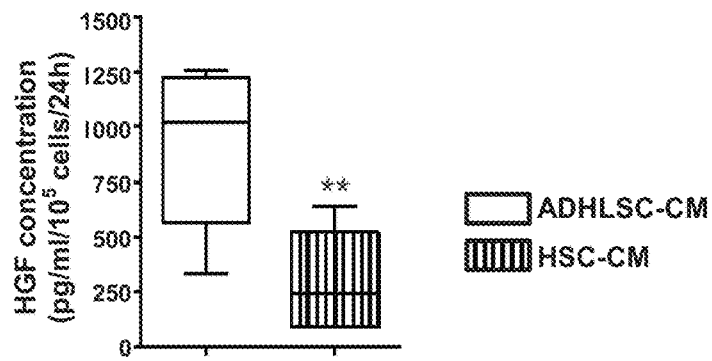
FIGS. 1A-1C: secretome profile in the conditioned culture medium of adult-derived human liver stem/progenitor cells (ADHLSC-CM) and hepatic stellate cells (HSC-CM) in absence of serum. HGF secretion is significantly higher in ADHLSC-CM (FIG. 1A) but a broader analysis of growth factors and cytokines secretion in ADHLSC-CM and HSC-CM shows many other proteins are more secreted in ADHLSC-CM (FIGS. 1B-1C). For the analysis of statistically relevant differences between ADHLSC-CM and HSC-CM, * denotes a p value <0.001,  denotes a p value <0.01, and * denotes a p value <0.05. ns: not significant.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +1-5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any $\geq 3$, $\geq 4$, $\geq 5$, $\geq 6$ or $\geq 7$ etc. of said members, and up to all said members. In another example, "one or more" or "at least one" may refer to 1, 2, 3, 4, 5, 6, 7 or more.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

As illustrated for representative non-limiting embodiments of the invention in the experimental section, the present inventors realised that a cell-free composition obtained by culturing adult-derived human liver stem/progenitor cells (ADHLSC; WO2007/071339; Najimi M et al., 2007; Khuu D et al., 2012) in cell culture medium and isolating the resulting conditioned medium (ADHLSC-CM) has unexpectedly advantageous components and properties, such as anti-fibrotic effects. ADHLSC-CM, compositions based on ADHLSC-CM, and other related and derived products, can be used in cell culture processes or as a medicament, more particularly for the treatment of diseases involving organ injury, organ failure, or the pathological disruption, inflammation, degeneration, and/or proliferation of cells within a tissue or an organ, in particular within liver.

The term "adult-derived human liver stem or progenitor cells", abbreviated as "ADHLSC", as used herein, specifically denotes the human progenitor or stem cell originated from human adult liver as disclosed in WO 2007/071339 and described in the relevant literature (Najimi et al. 2007; Khuu D et al., 2012), all incorporated by reference herein. Hence, the conditioned medium of ADHLSC as taught herein (ADHLSC-CM) is obtained by culturing ADHLSC.

Suitably, ADHLSC are obtained by using samples of adult liver, and are characterised by co-expression of at least one mesenchymal marker (preferably one, more than one or all of the markers CD90, CD73, CD44, vimentin and α-smooth muscle actin) with hepatic markers (preferably one or more of albumin, CD29, alpha-fetoprotein, alpha-1 antitrypsin, HNF-4 and MRP2 transporter). In particular ADHLSC typically co-express α-smooth muscle actin and/or vimentin and albumin (ALB), but are also characterized by other criteria such as the morphology (mesenchymal-like morphology with flattened form broad cytoplasm, growing in monolayers), the capability of differentiating into hepatocytes or hepatocyte-like cells and not differentiating into mesodermal cell types, and the lack of expression of other markers such cytokeratin-7, cytokeratin-19, Oct-4, CD45, CD34, CD133, and CD117. Thus, exemplary ADHLSC that can be used for obtaining ADHLSC-CM are albumin-positive, vimentin-positive, alpha smooth muscle actin-positive, cytokeratin-19-negative, and CD133-negative.

By means of further guidance, ADHLSC may be characterised in that it co-expresses at least one mesenchymal marker with the hepatocyte marker albumin (ALB). More particularly, ADHLSC may co-express α-smooth muscle actin (ASMA) and ALB. Even more particularly, ADHLSC may co-express vimentin, ASMA and ALB. Still more particularly, ADHLSC may co-express ASMA and ALB, or vimentin, ASMA and ALB, and be negative for cytokeratin-19 (CK-19). Negativity of ADHLSC for CK-19 may be particularly determined at protein level, e.g., by immunocytochemistry. Yet more particularly, ADHLSC may express CD90, CD73, CD44, vimentin, ASMA and ALB, and be negative for CK-19. ADHLSC typically also expresses further markers, such as CD29, CD13, cytochrome P450 3A4 (CYP3A4), CYP1B1, alpha fetoprotein (AFP), and alpha-anti-trypsin. In a particular example, ADHLSC may thus be characterised as CD90, CD29 and CD44 positive, albumin-positive, vimentin-positive and ASMA-positive, and negative for CD45, CD34, CD117 and CK-19. In another example, ADHLSC may be characterised as expressing CD90, CD73, CD29, CD44, CD13, vimentin, ASMA, ALB, AFP, CYP3A4 and alpha-anti-trypsin. In a further example, ADHLSC may be characterised as expressing CD90, CD73, CD29, CD44, CD13, vimentin, ASMA, ALB, AFP, CYP3A4 and alpha-anti-trypsin, and negative for CK-19 and CK-7. In a yet further example, ADHLSC may be characterised as expressing CD90, CD73, CD29, CD44, CD13, vimentin, ASMA, ALB, AFP, CYP3A4 and alpha-anti-trypsin, and negative for CK-19, CK-7, CD133, CD117, CD45, CD34 and HLA-DR. Positivity and negativity of ADHLSC for the various markers may be preferably determined at protein level, e.g., by immunocytochemistry. By means of example and without limitation, ADHLSC may display marker expression profile as found in the cells as deposited by Université catholique de Louvain (represented by Professor Bernard Coulie, Rector of UCL from 2004 to 2009) on Feb. 20, 2006 under the Budapest Treaty with the Belgian Coordinated Collections of Microorganisms (BCCM/LMBP) under accession number LMBP 6452CB. It shall be appreciated that cell lines derived of ADHLSC cells are also encompassed in the term.

Wherein a cell is said to be positive for (or to express, i.e., comprise expression of) a particular marker, this means that a skilled person will conclude the presence or evidence of a distinct signal, e.g., antibody-detectable (e.g., immunocytochemistry or immunoblotting) for that marker when carrying out the appropriate measurement, compared to suitable (negative) controls. Where the method allows for quantitative assessment of the marker, positive cells may on average generate a signal that is significantly different from the control, e.g., but without limitation, at least 1.5-fold higher than such signal generated by control cells, e.g., at least 4-fold, at least 5-fold, or at least 10-fold higher, or (preferably) even higher.

The expression of the above cell-specific markers can be detected using any suitable immunological technique known in the art (such as immuno-cytochemistry or affinity adsorption, Western blot analysis, FACS, ELISA, protein microarrays, etc.) or any suitable sequencing technologies for identifying and quantifying proteins from biological samples. Sequence data for markers listed in this disclosure are known and can be obtained from public databases such as GenBank (http://www.ncbi.nlm.nih.gov/) or Uniprot (http://www.uniprot.org).

By means of further guidance, the terms "progenitor" or "progenitor cell" are synonymous and generally refer to an unspecialised or relatively less specialised and proliferation-competent cell which can under appropriate conditions give rise to at least one relatively more specialised cell type, such as inter alia to relatively more specialised progenitor cells or eventually to terminally differentiated cells. A progenitor cell may "give rise" to another, relatively more specialised cell when, for example, the progenitor cell differentiates to become said other cell without previously undergoing cell division, or if said other cell is produced after one or more rounds of cell division and/or differentiation of the progenitor cell.

The term "stem cell" generally refers to a progenitor cell capable of self-renewal, i.e., which can under appropriate conditions proliferate without differentiation. The term encompasses stem cells capable of substantially unlimited self-renewal, i.e., wherein at least a portion of the stem cell's progeny substantially retains the unspecialised or relatively less specialised phenotype, the differentiation potential, and the proliferation capacity of the mother stem cell; as well as stem cells which display limited self-renewal, i.e., wherein the capacity of the stem cell's progeny for further proliferation and/or differentiation is demonstrably reduced compared to the mother cell.

The term "adult stem or progenitor cell" as used herein refers to a stem or progenitor cell present in or obtained from (such as isolated from) an organism at the foetal stage or after birth, such as for example at any one of the stages commonly referred to as "newborn", "infant", "child", "youth", "adolescent" or "adult". For example, ADHLSC may be originated from human foetuses, or from human subjects at any time after birth, preferably full term, e.g., 0-1 month of age after birth, or at least 1 month of age after birth, e.g., at least 2 months, at least 3 months, e.g., at least 4 months, at least 5 months, e.g., at least 6 months age after birth, such as, for example, 1 year or more, 5 years or more, at least 10 years or more, 15 years or more, 20 years or more, or 25 years or more of age after birth.

ADHLSC can be suitably isolated from human liver by the methods taught in WO 2007/071339 and further described by Najimi et al. 2007, both incorporated by reference herein.

ADHLSC can be also suitably genetically modified before being used for producing ADHLSC-CM by the methods taught in WO 2007/071339, in particular for increasing the replicative capacity of ADHLSC, for enhancing ADHLSC growth and/or activity, for constitutively or inducibly over-expressing a polypeptide normally expressed (and secreted, or not) by hepatocytes, an antibody, or a hormone.

Hence, ADHLSC is obtainable or directly obtained by a method comprising: (a) disassociating adult liver or a part thereof to obtain a population of primary cells from the said adult liver or part thereof, (b) plating the primary cell population onto a substrate which allows adherence of cells thereto, and (c) culturing cells from the primary cell population, which have adhered to the said substrate, for at least 7 days, preferably at least 10, at least 13, or at least 15 days until the cultured cell population is at least 40% and preferably at least 70% confluent, thereby allowing for the emergence and proliferation of the stem/progenitor cells in the cell population; and (d) increasing the proportion of the progenitor or stem cells in the cell population by passaging the cell population at least once and preferably at least two times, thereby preferably obtaining a substantially homogeneous population of the stem/progenitor cells. In step (b) preferably the liver parenchymal cell population is plated. Typically, the cell population may be passaged between 2 and 8 times in step (d), during which ADHLSC are expanded and produce ADHLSC-CM that can be isolated and characterized.

In a particular example, the method may comprise: (a) disassociating human adult liver or a part thereof to form a population of primary cells from the said adult liver or part thereof, (b) plating the primary cell population onto a substrate which allows adherence of cells thereto, (c) culturing cells from the primary cell population, which have adhered to the said substrate, for at least 7 days in a culture medium comprising serum and a combination of at least two exogenously added growth factors chosen from epidermal growth factor (EGF), dexamethasone, and insulin, preferably at least dexamethasone and insulin, more preferably dexamethasone and insulin but not EGF, and (d) exchanging the medium for basal medium comprising high glucose at a concentration between 3 000 mg/L and 6 000 mg/L and further culturing the cells, whereby ADHLSC emerges and proliferates. In step (b) preferably the liver parenchymal cell population is plated. Emergence of ADHLSC may be facilitated by allowing the cells to become about 70% confluent and passaging the cells at least once, and typically between 2 and 8 times.

In another example, the method may comprise: (a) disassociating, preferably by two-step collagenase method, adult liver or a part thereof from a human subject, to form a population of primary cells from the said adult liver or part thereof; (b) plating the primary cell population onto collagen type I coated substrate in Williams Medium E comprising foetal calf serum, preferably 10% (v/v), EGF, preferably 25 ng/ml, insulin, preferably 10 pg/ml, and dexamethasone, preferably 1 µM; (c) allowing adherence of cells from the primary cell population to the said substrate for 24 hours and thereafter exchanging the medium for fresh medium having composition as in (b); (d) culturing the cells in the said medium of (c) during two weeks, preferably 15 days; (e) exchanging the medium for DMEM comprising high glucose and FCS, preferably 10%, and further culturing the cells, whereby the progenitor or stem cells of the invention emerge and proliferate; (f) allowing the cells to become about 70% confluent and passaging the cells at least once and preferably at least two times, wherein the cells are plated onto the substrate as in (b) and cultured in a medium as in (e). In step (b) preferably the liver parenchymal cell population is plated. Typically, the cell population may be passaged between 2 and 8 times in step (f).

It shall be appreciated that in the above methods, more specifically during culturing and passaging the cells, the emerging ADHLSC cells become gradually overrepresented in the cell population, until a substantially homogeneous population of ADHLSC results. This process thus does not entail selection of individual colonies of cells in these steps.

The specific example as described by Najimi et al. 2007 (supra) is as follows. Single cell suspensions were resuspended in Williams' E medium (Invitrogen) supplemented with 10% foetal calf serum (FCS) (Perbio, Hyclone), 25 ng/ml EGF (Peprotech), 10 µg/ml insulin, 1 µM dexamethasone, and 1% penicillin/streptomycin (P/S) (Invitrogen). The cells were plated on six-well rat tail collagen I-coated plates (Greiner Bio-one) and cultured at 37° C. in a fully humidified atmosphere containing 5% CO2. After 24 h, medium was changed in order to eliminate the non-adherent cells and thereafter renewed every 3 days whereas the culture was microscopically followed every day. Culture medium was then switched to DMEM with high glucose concentrations (Invitrogen) supplemented with 10% FCS and 1% P/S in order to accelerate the elimination of hepatocytes. A cell type with mesenchymal-like morphology then spontaneously emerged, proliferated, and filled the empty space in the well plate as observed by phase contrast microscopy. When reaching 70% confluence, cells were lifted with 0.25% trypsin and 1 mM EDTA and re-plated at a density of $1 \times 10^4$ cells/cm$^2$. ADHLSC cells from third to eight passage were characterised further.

Hence, in certain embodiments, ADHLSC may be obtainable by or directly obtained by any of the above methods.

Accordingly, a method for producing a cell-free conditioned medium as taught herein may comprise the step of obtaining ADHLSC by any of the above methods, culturing ADHLSC in a cell culture medium, and separating the cell culture medium from ADHLSC.

The synonymous phrases "cell-free" and "free of cells" are generally well-understood, and in the present context may particularly signify that a composition such as a conditioned medium essentially does not contain (ADHLSC) cells, especially essentially does not contain viable (ADHLSC) cells. The degree to which a composition such as a conditioned medium is free of cells tends to be largely determined by the effectiveness of available methods for separating cells from culture media, such as, for example, centrifugation or filtration, or repetitions and/or combinations of such methods. For practical purposes, a composition such as a conditioned medium may be considered cell-free when it contains $5 \times 10^2$ or fewer cells/ml, preferably 100 or fewer cells/ml, more preferably 50 or fewer cells/ml, even more preferably 25 or fewer cells/ml, yet more preferably 10 or fewer cells/ml, still more preferably 10 or fewer cells/ml or 5 or fewer cells/ml, and most preferably no (i.e., 0) cells/ml; preferably these counts denote viable cells. Conventional cell counting methods may be used, such as light microscopy, or flow cytometry, or plating and colony forming units (CFU) determination. Conventional cell viability determination methods may be used, such as dye (e.g., trypan blue or propidium iodide) exclusion assays.

The term "medium" as used herein broadly encompasses any cell culture medium conducive to maintenance and/or proliferation of cells; more particularly conducive to maintenance of ADHLSC, preferably conducive to proliferation of ADHLSC. Typically, the medium will be a liquid culture medium, which facilitates easy manipulation (e.g., decantation, pipetting, centrifugation, filtration, and such) thereof.

Suitable culture medium is defined in the specific references (WO2007/071339; Khuu D et al., 2012) and in the Examples but it can be adapted for obtaining the enrichment (or the depletion) of specific elements. For example, ADHLSC-CM can be obtained by using serum-free medium and/or in presence or absence of specific nutrients. The density and the number of ADHLSC in the cell culture can be adapted to the desired volume and/or protein concentration of the ADHLSC-CM.

Typically, the medium will comprise a basal medium formulation as known in the art. Many basal media formulations (available, e.g., from the American Type Culture Collection, ATCC; or from Invitrogen, Carlsbad, Calif.) can be used to culture ADHLSC cells herein, including but not limited to Eagle's Minimum Essential Medium (MEM), Dulbecco's Modified Eagle's Medium (DMEM), alpha modified Minimum Essential Medium (alpha-MEM), Basal Medium Essential (BME), Iscove's Modified Dulbecco's Medium (IMDM), BGJb medium, F-12 Nutrient Mixture (Ham), Leibovitz L-15, DMEM/F-12, Essential Modified Eagle's Medium (EMEM), RPMI-1640, Medium 199, Waymouth's MB 752/1 or Williams Medium E, and modifications and/or combinations thereof. Compositions of the above basal media are generally known in the art and it is within the skill of one in the art to modify or modulate concentrations of media and/or media supplements as necessary for the cells cultured. A particularly preferred basal medium, especially for culturing ADHLSC, may be DMEM.

Such basal media formulations contain ingredients necessary for mammalian cell maintenance and proliferation, which are known per se. By means of illustration and not limitation, these ingredients may include inorganic salts (in particular salts containing Na, K, Mg, Ca, Cl, P and possibly Cu, Fe, Se and Zn), physiological buffers (e.g., HEPES, bicarbonate), nucleotides, nucleosides and/or nucleic acid bases, ribose, deoxyribose, amino acids, vitamins, antioxidants (e.g., glutathione) and sources of carbon (e.g., glucose, sodium pyruvate, sodium acetate), etc.

By means of example, a medium for culturing mammalian cells such as ADHLSC may contain between 1.0 g/L and 10.0 g/L D-glucose, preferably between 3.0 g/L and 6.0 g/L D-glucose, more preferably between 4.0 g/L and 5.0 g/L D-glucose, and most preferably 4.50 g/L glucose.

For use in culture, basal media can be supplied with one or more further components. For example, additional supplements can be used to supply the cells with the necessary trace elements and substances for optimal ADHLSC maintenance, growth, and/or expansion. Furthermore, antioxidant supplements may be added at appropriate concentrations, e.g., β-mercaptoethanol or N-acetyl-L-cysteine. While many basal media already contain amino acids, some amino acids may be supplemented later, e.g., L-glutamine, which is known to be less stable when in solution. A medium may be further supplied with antibiotic and/or antimycotic compounds, such as, typically, mixtures of penicillin and streptomycin, and/or other compounds, exemplified but not limited to, amphotericin, ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Lipids and lipid carriers can also be used to supplement cell culture media. Such lipids and carriers can include, but are not limited to cyclodextrin, cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. Albumin can similarly be used in fatty-acid free formulations.

Also contemplated is supplementation of cell culture media with mammalian plasma or sera.

Plasma or sera often contain cellular factors and components that facilitate cell viability and expansion. Optionally, plasma or serum may be heat inactivated. Heat inactivation is used in the art mainly to remove the complement. Heat inactivation typically involves incubating the plasma or serum at 56° C. for 30 to 60 min, e.g., 30 min, with steady mixing, after which the plasma or serum is allowed to gradually cool to ambient temperature. A skilled person will be aware of any common modifications and requirements of the above procedure. Optionally, plasma or serum may be sterilised prior to storage or use. Usual means of sterilisation may involve, e.g., filtration through one or more filters with pore size smaller than 1 μm, preferably smaller than 0.5 μm, e.g., smaller than 0.45 μm, 0.40 μm, 0.35 μm, 0.30 μm or 0.25 μm, more preferably 0.2 μm or smaller, e.g., 0.15 μm or smaller, 0.10 μm or smaller. Suitable sera or plasmas for use in media as taught herein may include human serum or plasma, or serum or plasma from non-human animals, preferably non-human mammals, such as, e.g., non-human primates (e.g., lemurs, monkeys, apes), foetal or adult bovine, horse, porcine, lamb, goat, dog, rabbit, mouse or rat serum or plasma, etc, or any combination of such. In certain preferred embodiments, a medium as taught herein may comprise bovine serum or plasma, preferably foetal bovine (calf) serum or plasma, more preferably foetal bovine (calf) serum (FCS or FBS). In other preferred embodiments, media as taught herein may comprise human serum or plasma, such as autologous or allogeneic human serum or plasma, preferably human serum, such as autologous or allogeneic human serum, more preferably autologous human serum or plasma, even more preferably autologous human serum.

In certain preferred embodiments, serum or plasma can be substituted in media as taught herein by serum replacements, such as to provide for serum-free media (i.e., chemically defined media). The provision of serum-free media may be advantageous particularly with view to administration of the media or fraction(s) thereof to subjects, especially to human subjects (e.g., improved bio-safety). By the term "serum replacement" it is broadly meant any a composition that may be used to replace the functions (e.g., cell maintenance and growth supportive function) of animal serum in a cell culture medium. A conventional serum replacement may typically comprise vitamins, albumin, lipids, amino acids, transferrin, antioxidants, insulin and trace elements. Many commercialized serum replacement additives, such as KnockOut Serum Replacement (KOSR), N2, B27, Insulin-Transferrin-Selenium Supplement (ITS), and G5 are well known and are readily available to those skilled in the art.

Plasma or serum or serum replacement may be comprised in media as taught herein at a proportion (volume of plasma or serum or serum replacement/volume of medium) between about 0.5% v/v and about 40.0% v/v, preferably between about 5.0% v/v and about 20.0% v/v, e.g., between about 5.0% v/v and about 15.0% v/v, more preferably between about 8.0% v/v and about 12.0% v/v, e.g., about 10.0% v/v.

A particularly preferred medium, especially for culturing ADHLSC, may be DMEM containing between 3.0 g/L and 6.0 g/L D-glucose, more preferably between 4.0 g/L and 5.0 g/L D-glucose, most preferably 4.50 g/L glucose; supplemented with between 5.0% v/v and 15.0% v/v foetal calf serum (FCS), preferably between 8.0% v/v and 12.0% v/v FCS, most preferably 10.0% v/v FCS; and suitably supplemented with antibiotics, e.g., penicillin and streptomycin. FCS is preferably substituted by a suitable amount of serum-replacement.

The term "conditioned medium" refers to a medium that has been exposed to (i.e., contacted with, cultured with) cells grown in culture for a time sufficient to include at least one additional component in the medium, said component produced by the cells, that was not present in the medium before exposing the same to the cells. In other words, a "conditioned medium" may be deemed as a composition comprising cell secretion products, such as inter alia cell secretion proteins and cellular metabolites, which has previously supported the maintenance and/or the proliferation of cells.

The period of time sufficient to include said at least one additional component in the medium may in particular be sufficient to achieve secretion by ADHLSC of mixed secretion products (including secreted proteins and microvesicles) into the medium. By means of example, said period of time may be at least about 1 hour, preferably at least about 3 hours, more preferably at least about 6 hours, even more preferably at least about 12 hours, still more preferably at least about 18 hours, and yet more preferably at least about 24 hours, such as for example at least about 36 hours or at least about 48 hours. Typically, said period of time will be no more than about 72 hours, more typically no more than about 60 hours, even more typically no more than about 48 hours.

A conditioned medium such as ADHLSC-CM may thus be obtainable by or directly obtained by culturing ADHLSC in a cell culture medium, thereby conditioning the medium, and separating the cell culture medium from the cells, thereby obtaining the conditioned medium. The terms "culturing" or "cell culture" are common in the art and broadly refer to maintenance of cells and potentially proliferation of cells in vitro. Typically, animal cells, such as mammalian cells, such as human cells, are cultured by exposing them to (i.e., contacting them with) a suitable cell culture medium in a vessel or container adequate for the purpose of an experiment (e.g., a 96-, 24-, or 6-well plate, a T-25, T-75, T-150 or T-225 flask, or a cell factory), at art-known conditions conducive to in vitro cell culture, such as temperature of 37° C., 5% v/v $CO_2$ and >95% humidity.

Regarding cell culture conditions, the material for cell culture (e.g., plates, flasks, or bioreactors) can be selected among those defined in WO2007/071339, or made available more recently and identified as adapted for growing cells like MSC or other primary cells in particular using conditions that make possible to generate ADHLSC-CM according to Good Manufacturing Practice requirements for cell-based pharmaceutical products. Preferably, any appropriate coating, treatment or other method for preparing the surface where primary cells or MSC (and ADHLSC in particular) adhere and proliferate can be used. For example, the surface can be coated with biological materials such as extracellular matrix attachment and adhesion proteins (e.g. collagen, laminin, fibronectin, heparin sulfate, hyaluronidate, or chondroitin sulfate, either applied individually or as mixtures), matrices (e. g. Matrigel™; BD Biosciences). Otherwise, pre-treated surface (such as CELLBIND™ cell culture materials, Ultra-Web® Synthetic Surfaces, or surfaces treated with synthetic peptides) can be used. Other cell culture conditions that can be finely adapted for obtaining ADHLSC-CM having the desired composition and properties include temperature, cell density at seeding, and oxygen tension.

The term "in vitro" generally denotes outside, or external to, animal or human body. The term "ex vivo" typically refers to tissues or cells removed from an animal or human body and maintained or propagated outside the body, e.g., in a culture vessel. The term "in vitro" as used herein should be understood to include "ex vivo". The term "in vivo" generally denotes inside, on, or internal to, animal or human body.

When preparing a conditioned medium, cells by the action of which the medium is to be conditioned may be contacted with the medium at variety of initial cell densities. By means of example, adherent cells, i.e., cells capable of adhering to tissue culture plastic or to suitable adherent substrate(s), such as ADHLSC, may be contacted with the medium at initial cell confluence of at least about 50%, e.g., at least about 55%, or of at least about 60%, e.g., at least about 65%, or of at least about 70%, e.g., at least about 75%, or of at least about 80%, e.g., at least about 85%, or of at least about 90%, e.g., at least about 95%, such as 96%, 97%, 98%, 99%, or even 100% initial cell confluence. The term "confluence" refers to density of cultured cells in which the cells contact one another covering substantially all of the surfaces available for cell proliferation (i.e., fully confluent).

By means of example, adherent cells, such as ADHLSC, may be contacted with the medium at initial cell density of at least about 1000 cells/$cm^2$ growth surface area, e.g., of at least about 10 000 cells/$cm^2$, or of at least about 25 000 cells/$cm^2$, or of at least about 50000 cells/$cm^2$ growth surface area, e.g., at least about 75 000 cells/$cm^2$, or of at least about 100 000 cells/$cm^2$, e.g., at least about 125 000 cells/$cm^2$ initial cell density. For example, adherent cells, such as ADHLSC, may be contacted with the medium at initial cell density of no more than about 200 000 cells/$cm^2$, typically no more than about 175 000 cells/$cm^2$, more typically no more than about 150 000 cells/$cm^2$ initial cell density. Hence, by means of example, adherent cells, such as ADHLSC, may usually be contacted with the medium at initial cell density of between about 50 000 cells/$cm^2$ and about 125 000 cells/$cm^2$, such as, e.g., between about 75 000 cells/$cm^2$ and about 100 000 cells/$cm^2$, such as, e.g., about 80 000 cells/$cm^2$.

When preparing a conditioned medium, the medium to be conditioned may be provided at volumes commonplace in tissue culture. Typically, adherent cells, such as ADHLSC, may be contacted with between about 0.10 mL/$cm^2$ growth surface area and about 0.40 mL/$cm^2$ growth surface area of medium, more typically between about 0.15 mL/$cm^2$ and about 0.35 mL/$cm^2$, even more typically between about 0.20 mL/$cm^2$ and about 0.30 mL/$cm^2$.

In certain embodiments, particularly but without limitation when the conditioned medium or product(s) derived there from are intended for administration to subjects, especially to human subjects, the medium may lack xenogeneic serum or plasma, i.e., serum or plasma originating from an organism of a species distinct from the species of the subject to which the conditioned medium or product(s) derived there from are to be administered. In an example, any plasma or serum contained in the medium may only be allogeneic serum or plasma, i.e., serum or plasma originating from a member of the same species as the species of the subject to which the conditioned medium or product(s) derived there from are to be administered, but not from the subject. In another example, any plasma or serum contained in the medium may only be autologous serum or plasma, i.e., serum or plasma originating from the subject to which the conditioned medium or product(s) derived there from are to be administered. In yet another, particularly preferred example, the medium may lack any serum or plasma, i.e., serum-free medium. The provision of media of these embodiments can improve the bio-safety and/or immunological profile of the medium.

The method for producing a cell-free conditioned medium may thus comprise the steps of culturing ADHLSC, that in particular co-express at least one mesenchymal marker selected from CD90, CD73, CD44, vimentin and α-smooth muscle actin with at least an hepatic marker selected from albumin, CD29, alpha-fetoprotein, alpha-1 antitrypsin, HNF-4 and MRP2 transporter, in a cell culture medium and separating the cell culture medium from ADHLSC. This method can be performed by using a cell culture medium that is a serum-free medium, by modifying specific conditions of cell culture, and/or by separating the cell culture medium from ADHLSC after culturing ADHLSC at given time points (e.g. at least 2 hours, at least 4 hours, at least 6 hours, at least 8 hours, at least 12 hours, or at least 24 hours) at the scope of obtaining ADHLSC-CM having a composition enriched (or depleted) in soluble proteins and/or microvesicles that are either degradated (or unstable) within the conditioned media or secreted by ADHLSC not in regular manner but only before or after a certain number of hours (and thus not progressively accumulated in the ADHLSC-CM). Relevant time points can be very short (e.g. 2 hours or less) or longer such as at 24 hours (as in the Examples), at 36 hours or more hours. By obtaining samples of ADHLSC-CM at these time points or at intermediate ones (such as 1 hour, 2 hours, 4 hours, 6 hours, 8 hours, 12 hours, or 18 hours) and testing such samples for their composition and/or activities, the optimal timing for obtaining the desired ADHLSC-CM can be determined.

In certain further embodiments, particularly but without limitation when the conditioned medium or product(s) derived there from are intended for administration to subjects, especially to human subjects, the medium may be manufactured such as to ensure compliance with good manufacturing practice (GMP) guidelines. In certain embodiments, the conditioned medium may be sterilised, such as conveniently by passing through a microbiological filter having pore size about 0.20 μm, e.g., between 0.20 μm and 0.25 μm, e.g., 0.21 μm, 0.22 μm, 0.23 μm, or 0.24 μm.

A conditioned medium may be separated from cells used to condition the medium by any available technique. Conventional techniques include for example removal of the medium from a culture vessel by decantation or pipetting, centrifugation of the medium to pellet cells, cell fragments and particulates present therein (e.g., centrifugation at between about 100×g and about 2 000×g, such as between about 500×g and about 1 500×g, such as at about 1 000×g, for between about 5 min and about 30 min, such as between about 10 min and 20 min, such as for about 15 min), filtration of the medium to filter away cells, cell fragments and particulates present therein (e.g., filtration through a standard microbiological filter having pore size about 1.0 μm or less, preferably about 0.8 μm or less, more preferably about 0.6 μm or less, yet more preferably about 0.4 μm or less, such as preferably about 0.2 μm). It shall be appreciated that repetitions and/or combinations of such methods may be employed to attain comparatively more complete separation.

Hence, the separation of ADHLSC-CM from ADHLSC can be performed by simply transferring the supernatant of the ADHLSC culture container (by decantation or pipetting) into a separate container and, optionally, repeating and/or combining filtration (e.g., filtration through a standard microbiological filter having pore size about 1.0 μm or less, preferably about 0.8 μm or less, more preferably about 0.6 μm or less, yet more preferably about 0.4 μm or less, such as preferably about 0.2 μm) or shortly centrifugation this cell culture supernatant at low speed (e.g., centrifugation at between about 100×g and about 2 000×g, such as between about 500×g and about 1 500×g, such as at about 1 000×g, for between about 5 min and about 30 min, such as between about 10 min and 20 min, such as for about 15 min), at the scope of pelleting any remaining cell, cell debris, or particulate. In this manner, a cell-free preparation is obtained as supernatant of the centrifugation and it can be then used for determining identity and concentration of the biological molecules that are present, such as soluble proteins or microvesicles as defined below, and according to commonly available technology such as immunoassays, spectrometry, or enzymatic assays.

As set forth in the experimental section, the inventors demonstrated that in a co-culture system where ADHLSC were separated from Hepatic Stellate Cells (HSC) by a 0.4 μm pore PTFE membrane insert, ADHLSC exerted desirable effects on HSC. This illustrates that at least some secretion products of ADHLSC, which exert an effect on HSC, do pass through a filter having pore size of 0.4 μm. Accordingly, in certain embodiments, the conditioned medium may be filtered through a filter having pore size not smaller than about 0.4 μm, such as, for example, having pore size between about 0.4 μm and about 1.0 μm or less, preferably between about 0.4 μm and about 0.8 μm or less, more preferably between about 0.4 μm and about 0.6 μm or less, such as about 0.4 μm, e.g., 0.40 μm, 0.41 μm, 0.42 μm, 0.43 μm, 0.44 μm, or 0.45 μm.

In certain embodiments, the conditioned medium may be sterilised, such as conveniently by passing through a microbiological filter having pore size about 0.20 μm, e.g., between 0.20 μm and 0.25 μm, e.g., 0.21 μm, 0.22 μm, 0.23 μm, or 0.24 μm.

A further aspect of the invention provides a product derived from ADHLSC-CM, which is a cell-free composition that is obtainable by fractioning ADHLSC-CM ("ADHLSC-CM Fraction").

Hence, ADHLSC-CM can be used directly for assessing the biological activity or for any appropriate application, but can be used for obtaining a cell-free composition following further processing steps, such as fractionation or any other appropriate processing step that can be combined to allow obtaining cell-free compositions containing all (or in part) biological molecules secreted by ADHLSC into ADHLSC-CM, in particular using any appropriate protein separation technique.

The fractionation of ADHLSC-CM can be performed by filtration, for distinguishing between the components passing through the membrane and those retained. Depending on the features of the membrane and the desired composition and/or use, the fraction of interest can be either one or the other. For instance, by making use of membranes having a pore size of 0.4 μm, 0.2 μm or less, the fraction passing through the membrane will possibly enriched of soluble proteins and smaller microvesicles, meanwhile larger microvesicles will be retained by the membrane. Those two fractions can represent distinct cell-free compositions derived from ADHLSC-CM that can be tested and then used for different applications.

Other means for fractionating ADHLSC-CM involve enzymatically digesting the ADHLSC-CM (for eliminating specific components of ADHLSC-CM), centrifuging (especially at high speed, for pelleting specifically desired or undesired components of ADHLSC-CM), adsorbing (by suing heparin or other compound retaining specifically desired or undesired components of ADHLSC-CM), and/or separating by chromatography (including immunoaffinity chromatography, gel chromatography, ion exchange, metal chelate affinity chromatography, HPLC purification and hydrophobic interaction chromatography), using matrices or beads having specific size, hydrophobicity, and/or affinity for a ligand.

The ADHLSC-CM and ADHLSC-CM Fractions comprise soluble proteins, together or not with microvesicles. Such soluble proteins form specific combinations wherein the ratio between proteins and their absolute can vary. However, ADHLSC-CM particularly enriched in a series of growth factors and cytokines whose alone, or preferably in combination comprising part or all of them, contribute defining the basic composition and, at least in part, main biological activities of ADHLSC-CM. These soluble proteins are hepatocyte growth factor (HGF), vascular endothelial growth factor (VEGF), eotaxin (CCL11), interleukin-6 (IL-6), and interleukin-8 (IL-8). Each, some or all of them are present at a concentration of at least 1 ng/ml. Further soluble proteins that can be present at similar (but or lower concentrations) are selected from matrix metalloproteases (such MMP-2 and MMP-1), growth factors (such as GM-CSF or PDGF-bb), chemokines (such as RANTES or MIP-1a), and cytokines (such as IFN-gamma, TNF-alpha, IL-10 or other proteins belonging to the group of interleukins), and other that can be identified by separating and analysing ADHLSC-CM according to the affinity, activity, or size (e.g. below 3 kDa, 10 kDa, 20 kDa, or 50 kDa) of the proteins. Depending on the actual concentration of such soluble proteins within the ADHLSC-CM Fraction, it can be consequently used for purifying any of such proteins.

The identification of soluble proteins that are present in ADHLSC-CM and that characterize one or more of its biological and functional features, can be performed by using the technologies that are commonly applied for determining the secretome of a cell type or a cell population, in parallel to the general transcriptome and proteome, as described in the literature (Eichelbaum K et al. 2012; Mukherjee P and Mani S, 2013). In particular, major findings on the composition and activities of ADHLSC secretome as presented by ADHLSC-CM can be determined in connection to liver activities, as shown in the literature for other types of cell secretomes for treatments in liver-directed regenerative medicine (Wu X and Tao R, 2012; Khuu D et al., 2012; Puglisi M et al. 2011). Some of the liver-relevant activities of such secretomes that have been shown (at least in vitro) include the decrease of invasiveness of liver tumour cells (Li G et al., 2010; Cavallari C et al., 2013; Qiao L et al., 2008; WO 2011070001), responsiveness to inflammatory serum stimulation (Yagi H et al, 2009), or blocking epithelial-to-mesenchymal transition relevant for fibrotic activities (Ueno T et al., 2013).

When the ADHLSC-CM, as well as the cell-free compositions that are obtained by fractioning ADHLSC-CM, contains as well (or only) microvesicles, they can be characterized and, when appropriate, selected according their size (below 1, 0.8, 0.4 or 0.2 µm), molecular weight (above 100 kDa, 300 kDa, 500 kDa, or 1000 kDa), and/or composition (in terms of proteins, lipids, or nucleic acids) using technologies such as filtration, (ultra)centrifugation (e.g. at a g-force comprised between about 20,000 and 300,000 g, preferably between about 80,000 and 200,000 g) or chromatography.

The term "fraction" as used herein aims to broadly denote the result of a separation process, in which a mixture (e.g., a solid, liquid, solute or suspension) is divided up in, i.e., separated into, two or more smaller quantities ("fractions") in which the composition changes. Hence, the composition of a fraction is altered compared to, i.e., is distinct from, the composition of the mixture subjected to the fractionation.

Particularly intended herein are "active" fractions of the conditioned medium of ADHLSC ("ADHLSC-CM Fractions"), i.e., fractions which at least partly retain the desired activity or activities of the conditioned medium of ADHLSC. For example, an active fraction of ADHLSC-CM may retain some, e.g., one or more, but not all activities of ADHLSC-CM. In another example, an active fraction of ADHLSC-CM may retain all activities of ADHLSC-CM, but to a lesser degree than ADHLSC-CM. In yet another example, an active fraction of ADHLSC-CM may retain all activities of ADHLSC-CM, to the same degree as ADHLSC-CM. Retention of a given activity or activities in an ADHLSC-CM Fraction may be readily evaluated by suitable in vitro or in vivo assays.

As intended herein, a "fraction" of ADHLSC-CM may preferably still contain a plurality of components. For example, a "fraction" of ADHLSC-CM may preferably contain a plurality of, by means of example and without limitation, at least about 5, or at least about 10, or at least about 20, or at least about 30, or at least about 40, or at least about 50, or at least about 100 or more distinct soluble proteins.

By means of further explanation, any known fractionation methods may be used to fractionate ADHLSC-CM. For example, protein constituents may be separated from ADHLSC-CM as a protein fraction using standard methods, such as centrifugation and ultracentrifugation to remove membraneous structures and large nucleic acids, and nuclease (DNAse, RNAse) treatment to remove nucleic acids. A fraction enriched for or comprising mainly (e.g., consisting essentially of or even consisting of) the protein constituents of the ADHLSC-CM can thereby be obtained. Such protein fraction may be further fractionated into two or more protein sub-fractions, for example based on any one or more of (1) charge (e.g., fractionation based on isoelectric point using pH graded gels or ion exchange columns), (2) size or molecular weight (e.g., fractionation using size exclusion chromatography or gel electrophoresis), (3) polarity/hydrophobicity (e.g., fractionation using high performance liquid chromatography or reversed-phase chromatography), (4) affinity to a substance (e.g., fractionation using immunoaffinity chromatography) or (5) heparin sulphate binding (e.g., fractionation using a heparin column). As intended herein, a fraction of ADHLSC secretion proteins may preferably still contain a plurality of components, e.g., a plurality of secretion proteins.

Such fractioning may thus comprise applying one or more technologies known in the art, such as for example filtering, enzymatically digesting, centrifuging, adsorbing, and/or separating by chromatography, to ADHLSC-CM.

Hence, also provided is an isolated fraction of the conditioned medium of ADHLSC, said fraction having composition distinct from the composition of the conditioned medium. A related aspect provides a method for producing the fraction of the conditioned medium of ADHLSC comprising isolating the fraction from the conditioned medium.

The term "isolated" with reference to a particular component generally denotes that such component exists in separation from—for example, has been separated from or prepared and/or maintained in separation from—one or more other components of its natural environment. The term "isolated" as used herein may preferably also encompass the qualifier "purified". By means of example, the term "purified" with reference to a substance does not require absolute purity. Instead, it denotes that such substance is in a discrete environment in which its abundance (conveniently expressed in terms of mass or weight or concentration) relative to other relevant substances is greater than in the material which was subjected to the purification. A discrete environment denotes a single medium, such as for example a single solution, gel, precipitate, lyophilisate, etc.

For example, microvesicles may be separated from ADHLSC-CM as a microvesicle fraction using standard methods. Cell-derived microvesicles (MV) are small vesicles released by cells that express the characteristic antigens of the cell from which they originate and carry membrane and cytoplasmic constituents and have been described as a new mechanism of cell communication. MV may contribute to tissue regeneration and repair. MV may be typically spheroid in shape with diameters within the range of 50 nm to 5 µm, more typically of between 0.2 and 1 µm. If the particle is not spheroid in shape, the above mentioned values are referred to the largest dimension of the particle. Microvesicles are shed from almost all cell types that originate directly from the plasma membrane of the cell and reflect the antigenic content of the cells from which they originate. Microvesicles can play a role in intercellular communication between cells, even at distant sites, and can transport mRNA, miRNA, and proteins that may have various effects on cells interacting with them, such as on immunomodulation or proliferation. Methods to isolate MV fraction may include ultracentrifugation, e.g., (repeated) ultracentrifugation of ADHLSC-CM at 100,000 g for 1 h at 4° C., and re-suspending the pellet in a suitable medium or buffer. An ADHLSC-CM fraction enriched for or comprising mainly (e.g., consisting essentially of or even consisting of) MV of the CM is thereby obtained.

Also provided herein is an isolated ADHLSC-CM Fraction of said mixed secretion proteins, said fraction having composition distinct from the composition of the mixed secretion proteins. The term "mixed secretion proteins" is used herein to conveniently refer to the collection or plurality of protein products of ADHLSC found in ADHLSC-CM.

The terms "peptide" and "polypeptide" refer to compounds made up of a single chain of amino acid residues linked by peptide bonds. The term "protein" as used herein may be synonymous with the terms "peptide" and "polypeptide" (i.e., the latter two terms are within the ambit of the term "protein") or may refer, in addition, to a polypeptide (a compound made up of a single chain of amino acid residues linked by peptide bonds) complexed with one or more same or other polypeptides. The complex may be held by non-covalent interactions and/or covalent bond(s), e.g., disulfide bonds, between the constituent polypeptides. In addition, the term "protein" may refer to peptides, polypeptides or proteins in which one or more amino acid residues are modified by post-translational modification, including, but not limited to glycosylation, phosphorylation, formation of intra- or inter-molecular disulphide bonds, and the like.

The phrase "mixed secretion proteins" is not to be deemed as an indication that the collection of proteins would be limited to those which have been secreted by the cells' secretion machinery. Instead, the phrase is intended to cover any cellular proteins that have entered the medium.

However, proteins that have been secreted by the cells' secretion machinery may constitute prominent and preferred members of the collection.

A preparation of isolated mixed microvesicles produced by ADHLSC represents an ADHLSC-CM Fraction, said fraction having a composition distinct from the composition of the initial ADHLSC-CM. The term "mixed microvesicles" is used herein to conveniently refer to the collection or plurality of microvesicles produced by ADHLSC, found in ADHLSC-CM, and preferably isolated as an ADHLSC-CM Fraction.

In certain embodiments, ADHLSC-CM or the ADHLSC-CM Fraction may be concentrated compared to the medium as directly separated from the cells used to condition it, or compared to the cell-free compositions that are obtained by fractioning ADHLSC-CM. For example, the products may be so concentrated at least about 5-fold, or at least about 10-fold, or at least about 15-fold, or at least about 20-fold, or at least about 25-fold, or at least about 50-fold, or at least about 100-fold. Any suitable technique may be employed to eliminate the excess of liquid components and concentrate the ADHLSC-CM or an ADHLSC-CM Fraction, such as without limitation ultrafiltration, evaporation, dialysis, lyophilisation, and the like. For example, the liquid products may be concentrated using ultrafiltration units for centrifugation with membranes having very small pore size and/or weight cut-off. Protein and other soluble components of the liquid products may be concentrated by using ultrafiltration units with a 3 kD molecular weight cut-off (Amicon Ultra-PL 3, Millipore, Bedford, Mass., USA). The liquid product that is concentrated by ultrafiltration retains most of its proteins and general biological activities due to its components not passing through the filter. Otherwise, by using larger cut-off and/or preliminary differential centrifugation steps, the concentration may be associated to a further fractionation of ADHLSC-CM or an ADHLSC-CM Fraction (e.g. by eliminating components of lower molecular size and weight).

In certain embodiments, ADHLSC-CM or an ADHLSC-CM Fraction, may be diluted compared to the medium as directly separated from the cells used to condition it, or compared to the cell-free compositions that are obtained by fractioning ADHLSC-CM. For example, the products may be so diluted at least about 5-fold, or at least about 10-fold, or at least about 15-fold, or at least about 20-fold, or at least about 25-fold. By means of example, the products may be so diluted not more than about 50-fold, e.g., not more than about 40-fold or not more than about 30-fold. Hence, by means of example the products may be so diluted between about 5-fold and about 50-fold, or between about 10-fold and about 40-fold, or between about 20-fold and about 30-fold, e.g., about 25-fold. The liquid products may be suitably diluted by admixing it with an aqueous solvent, e.g., distilled water, physiological solution (0.90% w/v of NaC), medium, buffer, and the like. The dilution, or the reconstitution of a previously lyophylized or otherwise (cryo-) preserved preparation of liquid products, can be performed by adding the required amount of non-conditioned media or any appropriate cell-free solution, such as a buffer (e.g. PBS) or other physiological solutions that are compatible with further uses (e.g. administration in a subject).

Hence, at any moment before, during, or after fractionation, the desired concentration of the soluble proteins and/or microvesicles within ADHLSC-CM or an ADHLSC-CM Fraction can be obtained by appropriately concentrating (or diluting) said preparation at least about 2-fold, at least about 5-fold, at least about 10-fold, at least about 20-fold, at least about 50-fold, at least about 100-fold, or in any appropriate intermediate manner (e.g. at least about 3-fold, 7-fold, 15-fold, 25-fold, 30-fold, or 75-fold). If needed, concentration and dilution steps may be alternated in order to obtain a product from ADHLSC-CM that present the appropriate activity, volume, and/or composition for further use.

Provided are also any of the aforementioned products, in particular ADHLSC-CM or an ADHLSC-CM Fraction, or their combinations with other product, which are suitable for therapeutic uses. Hence, an aspect provides the ADHLSC-CM or ADHLSC-CM Fractions, or any other suitable (combination of) product(s) disclosed herein, including combinations of such product(s) with ADHLSC or any other cell preparation that can be administered for obtaining a therapeutic activity, for use as a medicament. Given the diversity of useful actions of the products that are derived from ADHLSC-CM, such as their trophic, immuno-modulatory, and/or anti-fibrotic actions, they can provide benefits in a variety of medical indications, examples of which are set forth elsewhere in this specification.

If such ADHLSC-CM or ADHLSC-CM Fractions are tested initially without including other exogenous compounds, the addition of such compounds may be appropriate to have improved (if not synergistic) therapeutic effect at specific concentrations. A list of exogenous compounds being active ingredients that can be combined with ADHLSC-CM or an ADHLSC-CM Fraction include cells (in particular having liver origin and/or mesenchymal feature, such as ADHLSC or other cells suitable for ex vivo or in vivo applications), proteins (e.g., matrix metalloproteases, growth factors, chemokines, cytokines, hormones, antigens, or antibodies), nutrients (e.g., sugars or vitamins) and/or chemicals (e. g., drugs with immunomodulating, anti-fibrotic, antiviral or other therapeutic properties) that were not initially present in ADHLSC-CM or in an ADHLSC-CM Fraction and that are known to be effective as medicament for a given indication. The use of specific animal models and clinical data, as well as the understanding of the underlying biological mechanism, may contribute in defining which additional compounds can be added, at which concentration and, eventually, using which method or schedule of administration.

Accordingly, such medical, e.g., prophylactic or therapeutic, uses may involve using ADHLSC-CM, an ADHLSC-CM Fraction, or other suitable (combination of) product(s) as disclosed herein alone or in combination with one or more exogenous active ingredients, which may be suitably added.

The ADHLSC-CM or the ADHLSC-CM Fraction may be suitably formulated as pharmaceutical formulations comprising a pharmaceutically effective amount of any ADHLSC-CM or an ADHLSC-CM Fraction.

Accordingly, a further aspect provides pharmaceutical formulations comprising a pharmaceutically effective amount of ADHLSC-CM or an ADHLSC-CM Fraction or other suitable (combination of) product(s) as disclosed herein. The pharmaceutical formulations may optionally also further comprise a pharmaceutically effective amount of one or more exogenous active ingredients, which may be of the type discussed above, e.g., the cells, proteins, nutrients, and/or chemicals.

The pharmaceutical formulations may comprise one or more pharmaceutically acceptable excipients. The pharmaceutical formulations may be conveniently formulated into compositions or kits of parts.

The pharmaceutical formulations comprising a pharmaceutically effective amount of ADHLSC-CM or an ADHLSC-CM Fraction, may contain excipients and other compounds that allow the correct preservation, stability, or administration of the pharmaceutical composition. Moreover, a further pharmaceutically effective amount of one or more exogenous active ingredients (cells, proteins, nutrients and/or chemicals) may be provided in the pharmaceutical formulation according to the preliminary analysis defined as briefly described above.

The term "pharmaceutically acceptable" as used herein is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, antioxidants, tonicity controlling agents, absorption delaying agents, and the like. The use of such media and agents for pharmaceutical active substances is well known in the art. Except insofar as any conventional media or agent is incompatible with the active substance, its use in the therapeutic compositions may be contemplated.

Illustrative, non-limiting carriers for use in formulating the pharmaceutical compositions include, for example, oil-in-water or water-in-oil emulsions, aqueous compositions with or without inclusion of organic co-solvents suitable for intravenous (IV) use or for injections in other locations, liposomes or surfactant-containing vesicles, microspheres, microbeads and microsomes, powders, tablets, capsules, suppositories, aqueous suspensions, aerosols, and other carriers apparent to one of ordinary skill in the art.

Pharmaceutical compositions as intended herein, such as in particular the ADHLSC-CM or an ADHLSC-CM Fraction, can be formulated for essentially any route of administration, such as without limitation, oral administration (such as, e.g., oral ingestion or inhalation), intranasal administration (such as, e.g., intranasal inhalation or intranasal mucosal application), parenteral administration (such as, e.g., subcutaneous, intravenous, intramuscular, intrahepatic, intrasplenic, intraperitoneal or intrasternal injection or infusion), transdermal or transmucosal (such as, e.g., oral, sublingual, intranasal) administration, topical administration, rectal, vaginal or intra-tracheal instillation, and the like. In this way, the therapeutic effects attainable by the methods and compositions of the invention can be, for example, systemic, local, tissue-specific, etc., depending of the specific needs of a given application of the invention.

For example, for oral administration, pharmaceutical compositions may be formulated in the form of pills, tablets, lacquered tablets, coated (e.g., sugar-coated) tablets, granules, hard and soft gelatin capsules, aqueous, alcoholic or oily solutions, syrups, emulsions or suspensions. In an example, without limitation, preparation of oral dosage forms may be is suitably accomplished by uniformly and intimately blending together a suitable amount of the active compound in the form of a powder, optionally also including finely divided one or more solid carrier, and formulating the blend in a pill, tablet or a capsule. Exemplary but non-limiting solid carriers include calcium phosphate, magnesium stearate, talc, sugars (such as, e.g., glucose, mannose, lactose or sucrose), sugar alcohols (such as, e.g., mannitol), dextrin, starch, gelatin, cellulose, polyvinylpyrrolidine, low melting waxes and ion exchange resins. Compressed tablets containing the pharmaceutical composition can be prepared by uniformly and intimately mixing the active ingredient with a solid carrier such as described above to provide a mixture having the necessary compression properties, and then compacting the mixture in a suitable machine to the shape and size desired. Molded tablets maybe made by molding in a suitable machine, a mixture of powdered compound moistened with an inert liquid diluent. Suitable carriers for soft gelatin capsules and suppositories are, for example, fats, waxes, semisolid and liquid polyols, natural or hardened oils, etc.

For example, for oral or nasal aerosol or inhalation administration, pharmaceutical compositions may be formulated with illustrative carriers, such as, e.g., as in solution with saline, polyethylene glycol or glycols, DPPC, methylcellulose, or in mixture with powdered dispersing agents, further employing benzyl alcohol or other suitable preservatives, absorption promoters to enhance bioavailability, fluorocarbons, and/or other solubilising or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Illustratively, delivery may be by use of a single-use delivery device, a mist nebuliser, a breath-activated powder inhaler, an aerosol metered-dose inhaler (MDI) or any other of the numerous nebuliser delivery devices available in the art. Additionally, mist tents or direct administration through endotracheal tubes may also be used.

Examples of carriers for administration via mucosal surfaces depend upon the particular route, e.g., oral, sublingual, intranasal, etc. When administered orally, illustrative examples include pharmaceutical grades of mannitol, starch, lactose, magnesium stearate, sodium saccharide, cellulose, magnesium carbonate and the like, with mannitol being preferred. When administered intranasally, illustrative examples include polyethylene glycol, phospholipids, glycols and glycolipids, sucrose, and/or methylcellulose, powder suspensions with or without bulking agents such as lactose and preservatives such as benzalkonium chloride, EDTA. In a particularly illustrative embodiment, the phospholipid 1,2 dipalmitoyl-sn-glycero-3-phosphocholine (DPPC) is used as an isotonic aqueous carrier at about 0.01-0.2% for intranasal administration of the compound of the subject invention at a concentration of about 0.1 to 3.0 mg/ml.

For example, for parenteral administration, pharmaceutical compositions may be advantageously formulated as solutions, suspensions or emulsions with suitable solvents, diluents, solubilisers or emulsifiers, etc. Suitable solvents are, without limitation, water, physiological saline solution or alcohols, e.g. ethanol, propanol, glycerol, in addition also sugar solutions such as glucose, invert sugar, sucrose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. The agents and pharmaceutically acceptable salts thereof of the invention can also be lyophilised and the lyophilisates obtained used, for example, for the production of injection or infusion preparations. For example, one illustrative example of a carrier for intravenous use includes a mixture of 10% USP ethanol, 40% USP propylene glycol or polyethylene glycol 600 and the balance USP Water for Injection (WFI). Other illustrative carriers for intravenous use include 10% USP ethanol and USP WFI; 0.01-0.1% triethanolamine in USP WFI; or 0.01-0.2% dipalmitoyl diphosphatidylcholine in USP WFI; and 1-10% squalene or parenteral vegetable oil-in-water emulsion. Illustrative examples of carriers for subcutaneous or intramuscular use include phosphate buffered saline (PBS) solution, 5% dextrose in WFI and 0.01-0.1% triethanolamine in 5% dextrose or 0.9% sodium chloride in USP WFI, or a 1 to 2 or 1 to 4 mixture of 10% USP ethanol, 40% propylene glycol and the balance an acceptable isotonic solution such as 5% dextrose or 0.9% sodium chloride; or 0.01-0.2% dipalmitoyl diphosphatidylcholine in USP WFI and 1 to 10% squalene or parenteral vegetable oil-in-water emulsions.

Where aqueous formulations are preferred, such may comprise one or more surfactants. For example, the composition can be in the form of a micellar dispersion comprising at least one suitable surfactant, e.g., a phospholipid surfactant. Illustrative examples of phospholipids include diacyl phosphatidyl glycerols, such as dimyristoyl phosphatidyl glycerol (DPMG), dipalmitoyl phosphatidyl glycerol (DPPG), and distearoyl phosphatidyl glycerol (DSPG), diacyl phosphatidyl cholines, such as dimyristoyl phosphatidylcholine (DPMC), dipalmitoyl phosphatidylcholine (DPPC), and distearoyl phosphatidylcholine (DSPC); diacyl phosphatidic acids, such as dimyristoyl phosphatidic acid (DPMA), dipahnitoyl phosphatidic acid (DPPA), and distearoyl phosphatidic acid (DSPA); and diacyl phosphatidyl ethanolamines such as dimyristoyl phosphatidyl ethanolamine (DPME), dipalmitoyl phosphatidyl ethanolamine (DPPE) and distearoyl phosphatidyl ethanolamine (DSPE). Typically, a surfactant:active substance molar ratio in an aqueous formulation will be from about 10:1 to about 1:10, more typically from about 5:1 to about 1:5, however any effective amount of surfactant may be used in an aqueous formulation to best suit the specific objectives of interest.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquidify and/or dissolve in the rectal cavity to release the drug.

Suitable carriers for microcapsules, implants or rods are, for example, copolymers of glycolic acid and lactic acid.

One skilled in this art will recognize that the above description is illustrative rather than exhaustive. Indeed, many additional formulations techniques and pharmaceutically-acceptable excipients and carrier solutions are well-known to those skilled in the art, as is the development of suitable dosing and treatment regimens for using the particular compositions described herein in a variety of treatment regimens.

The dosage or amount of the present active substances used, optionally in combination with one or more other active compound to be administered, depends on the individual case and is, as is customary, to be adapted to the individual circumstances to achieve an optimum effect. Thus, it depends on the nature and the severity of the disorder to be treated, and also on the sex, age, body weight, general health, diet, mode and time of administration, and individual responsiveness of the human or animal to be treated, on the route of administration, efficacy, metabolic stability and duration of action of the compounds used, on whether the therapy is acute or chronic or prophylactic, or on whether other active compounds are administered in addition to the agent(s) of the invention.

Without limitation, depending on the type and severity of the disease, a typical daily dosage of a product as disclosed herein might range from about 1 µg/kg to 1 g/kg of body weight or more, depending on the factors mentioned above. For instance, a daily dosage of a product as disclosed herein may range from about 1 mg/kg to 1 g/kg of body weight. For repeated administrations over several days or longer, depending on the condition, the treatment is sustained until a desired suppression of disease symptoms occurs. Thus, one or more doses of about 10.0 mg/kg, 20.0 mg/kg, 50.0 mg/kg, 100 mg/kg, 200 mg/kg, 300 mg/kg, 400 mg/kg, or 500 mg/kg of body weight (or any combination thereof) may be administered to the patient. Such doses may be administered intermittently, e.g., every day, every other day, every week or every two or three weeks.

In certain embodiments, where the active ingredient comprises or consists of microvesicles, the pharmaceutical formulation may be in a dosage form suitable for administration of the microvesicles in an amount from about 1 to about 500 µg/kg, from about 10 to about 250 µg/kg, or from about 30 to about 120 µg/kg body weight.

The products as disclosed herein may be used alone or in combination with any other active ingredient useful in treating the condition being targeted ("combination therapy"). Combination therapies as contemplated herein may comprise the administration of at least one active substance of the present invention and at least one other pharmaceutically or biologically active ingredient. Said present active substance(s) and said pharmaceutically or biologically active ingredient(s) may be administered in either the same or different pharmaceutical formulation(s), simultaneously or sequentially in any order.

The present products and pharmaceutical compositions are useful for treating patients. The terms "subject" or "patient" are used interchangeably and refer to animals, preferably warm-blooded animals, more preferably vertebrates, even more preferably mammals, still more preferably primates, and most preferably human patients. The term "mammal" includes any animal classified as such, including, but not limited to, humans, domestic and farm animals, zoo animals, sport animals, pet animals, companion animals and experimental animals, such as, for example, mice, rats, hamsters, rabbits, dogs, cats, guinea pigs, cattle, cows, sheep, horses, pigs and primates, e.g., monkeys and apes. Particularly preferred are human subjects, including both genders and all age categories thereof. Non-human animal subjects may also include prenatal forms of animals, such as, e.g., embryos or foetuses. Human subjects may also include foetuses, but by preference not embryos.

As used herein, a phrase such as "a subject in need of treatment" includes subjects that would benefit from treatment of a given condition. Such subjects may include, without limitation, those that have been diagnosed with said condition, those prone to develop said condition and/or those in whom said condition is to be prevented.

The terms "treat" or "treatment" encompass both the therapeutic treatment of an already developed disease or condition, such as the therapy of an already developed proliferative disease, as well as prophylactic or preventive measures, wherein the aim is to prevent or lessen the chances of incidence of an undesired affliction, such as to prevent occurrence, development and progression of proliferative diseases. Beneficial or desired clinical results may include, without limitation, alleviation of one or more symptoms or one or more biological markers, diminishment of extent of disease, stabilised (i.e., not worsening) state of disease, delay or slowing of disease progression, amelioration or palliation of the disease state, and the like. "Treatment" can also mean prolonging survival as compared to expected survival if not receiving treatment.

The term "pharmaceutically effective amount" refers to an amount of an active compound or pharmaceutical agent that achieves a medicinal benefit in a subject, e.g., a prophylactic or therapeutic benefit. Hence, "prophylactically effective amount" refers to an amount of an active compound or pharmaceutical agent that inhibits or delays in a subject the onset of a disorder as being sought by a researcher, veterinarian, medical doctor or other clinician. The term "therapeutically effective amount" as used herein, refers to an amount of active compound or pharmaceutical agent that elicits the biological or medicinal response in a subject that is being sought by a researcher, veterinarian, medical doctor or other clinician, which may include inter alia alleviation of the symptoms of the disease or condition being treated. Methods are known in the art for determining therapeutically and prophylactically effective doses for the present products.

ADHLSC-CM and ADHLSC-CM Fractions may exert valuable therapeutic effects in a plurality of pathologies. In particular but without limitation, the trophic actions (e.g., regulation of cell survival, proliferation, growth and differentiation), the immuno-modulatory actions, and/or the anti-fibrosis actions of the products may play prominent roles.

The ADHLSC-CM or an ADHLSC-CM Fraction can be administered intravenously, (e.g. intraportally), intrahepatically, intrasplenically, or intraperitoneally, simultaneously or separately from other medicaments, as well as using a delivery system comprising a source of the selected cell-free composition together with a dispenser operable to deliver the conditioned medium to a target tissue or organ. The delivery system may involve culturing ADHLSC in an extracorporeal bioreactor (or any other appropriate device) comprising a fluid treatment compartment and a cell culture compartment, and a selectively permeable barrier (e.g. a membrane, an ultrafiltration cartridge or a bundle of hollow fibers) that separates the fluid treatment compartment and the cell compartment, wherein the cell culture compartment comprises ADHLSC. This system may further comprise a biological fluid inlet and a biological fluid outlet, wherein the biological fluid inlet and outlet permit fluid communication between the fluid treatment compartment and a bloodstream of the subject.

The ADHLSC-CM or an ADHLSC-CM Fraction, or other suitable (combination of) product(s) as disclosed herein, can be used in the treatment (as a prophylaxis or a therapy) of a series of disorders such as fibrotic disorders, liver disorders, organ injury or failure, or any other or the pathological disruption, inflammation, degeneration, and/or proliferation within an organ or a tissue. The ADHLSC-CM or of the cell-free compositions that are obtained by fractioning ADHLSC-CM can autologous to the subject (if ADHLSC from the same subject were used for producing ADHLSC-CM) or allogeneic to the subject (if ADHLSC from another subject were used for producing ADHLSC-CM).

Moreover, ADHLSC-CM or an ADHLSC-CM Fraction, or other suitable (combination of) product(s) as disclosed herein, can be used as supporting the transplantation of an organ (in particular liver) or cells (in particular, transplantation of ADHLSC, hepatocytes, or organ- and/or differentiation-specific MSC), as a subsidiary treatment that can be administered before, after, or when performing transplantation.

The ADHLSC-CM or an ADHLSC-CM Fraction, or other suitable (combination of) product(s) as disclosed herein, can be used in the treatment of organ injury or organ failure, preferably wherein the organ is liver, or for use in the treatment of excessive accumulation of fibrous tissue, preferably wherein excessive accumulation of fibrous tissue affects the liver, or for use in the treatment of a liver disease, or for use in the treatment of a proliferative disease, preferably wherein the proliferative disease affects the liver.

ADHLSC-CM or an ADHLSC-CM Fraction, or other suitable (combination of) product(s) as disclosed herein, may be also used for preventing or treating liver disorders, in particular those disorders involving the pathological disruption, inflammation, degeneration, and/or proliferation of liver cells, such as liver fibrotic disorders, liver failure, acute or chronic liver failure, acute liver infections, cholangitis, biliary cirrhosis. The liver fibrotic disorders may be associated, or caused by, diabetes, metabolic syndromes, viral hepatitis, chronic persistent or active hepatitis, autoimmune hepatitis, alcoholic liver disease, fatty liver disease, nonalcoholic steatohepatitis (NASH), acute-on-chronic liver failure (ACLF), primary biliary cirrhosis, primary sclerosing cholangitis, biliary atresia, congenital liver disease, hepatocellular carcinoma, or liver fibrosis coincident with chronic or repeated alcohol ingestion, with infection, with liver transplant, or with drug induced liver injury.

The ADHLSC-CM or an ADHLSC-CM Fraction, or other suitable (combination of) product(s) as disclosed herein, may be administered after that an initial diagnosis, risk assessment, or progression of the specific disease is established by analysis of biopsies or on the basis of the elevated level in the plasma of some markers of liver injury, dysfunction, fibrosis, alteration, or necrosis. These biochemical markers associated to liver activity and status can be selected among those disclosed in the literature and in particular Alanine aminotransferase (ALAT), Aspartate aminotransfersase (ASAT), Alkaline Phosphatase (AP), Gamma Glutamyl transpeptidase (GGT), Cytokeratin-18 (CK-18) or Resistin. In a particular embodiment, the liver disorder is a fatty liver disease in which the elevation of one or more of these markers is associated to a more or less significant steatosis in the liver, as it can be confirmed by a liver biopsy.

The ADHLSC-CM or an ADHLSC-CM Fraction, or other suitable (combination of) product(s) as disclosed herein, can be used for preventing or treating fibrotic disorders, including but not limited to liver fibrotic disorders, pulmonary fibrosis, kidney fibrosis, prostate fibrosis, breast fibrosis, heart muscle fibrosis and other disorders involving the increase specific markers of fibrosis, that is any biochemical, serological markers or any other clinical or echographic characteristics, that can be correlated with the presence of fibrotic disease. Examples of biochemical and serological markers include, yet are not limited to extracellular matrix components (such as laminin, tenascin, fibronectin, specific types of collagens).

Organ failure as intended herein may for example encompass liver failure, such as chronic liver failure and acute liver failure. By means of example and not limitation, liver failure occurs when large parts of the liver become damaged and the liver is no longer able to perform its normal physiological function. In some aspects, liver failure can be diagnosed using any assay of liver function. In some embodiments, liver failure can be diagnosed (e.g., initially diagnosed) based on a subject's symptoms. Symptoms that are associated with liver failure include, for example, one or more of the following, nausea, loss of appetite, fatigue, diarrhea, jaundice, abnormal/excessive bleeding (e.g., coagulopathy), swollen abdomen, mental disorientation or confusion (e.g., hepatic encephalopathy), sleepiness, and coma. Chronic liver failure occurs over months to years and is most commonly caused by viruses (e.g., HBV and HCV), long-term/excessive alcohol consumption, cirrhosis, hemochromatosis, and malnutrition.

Acute liver failure is the appearance of severe complications after the first signs of liver disease (e.g., jaundice). Acute liver failure includes a number of conditions, all of which involve severe hepatocyte injury or necrosis. In most cases of acute liver failure, massive necrosis of hepatocytes occurs; however, hepatocellular failure without necrosis is characteristic of fatty liver of pregnancy and Reye's syndrome. Altered mental status (hepatic encephalopathy) and coagulopathy in the setting of a hepatic disease generally define acute liver failure. Consequently, acute liver failure is generally clinically defined as the development of coagulopathy, usually an international normalized ratio (a measure of the time it takes blood to clot compared to an average value—INR) of greater than 1.5, and any degree of mental alteration (encephalopathy) in a patient without preexisting cirrhosis and with an illness of less than 26 weeks' duration.

Acute liver failure (or acute-on-chronic liver failure) indicates that the liver has sustained severe damage resulting in the dysfunction of 80-90% of liver cells.

Acute liver failure occurs when the liver fails rapidly. Hyperacute liver failure is characterized as failure of the liver within one week. Acute liver failure is characterized as the failure of the liver within 8-28 days. Subacute liver failure is characterized as the failure of the liver within 4-12 weeks. In some embodiments, the compositions and methods described herein are particularly suitable for the treatment of hyperacute, acute, and subacute liver failure, all of which are referred to herein as "acute liver failure." Common causes for acute liver failure include, for example, viral hepatitis, exposure to certain drugs and toxins (e.g., fluorinated hydrocarbons (e.g., trichloroethylene and tetrachloroethane), *Amanita phalloides* (e.g., commonly found in the "death-cap mushroom"), acetaminophen (paracetamol), halothanes, sulfonamides, henytoins), cardiac-related hepatic ischemia (e.g., myocardial infarction, cardiac arrest, cardiomyopathy, and pulmonary embolism), renal failure, occlusion of hepatic venous outflow (e.g., Budd-Chiari syndrome), Wilson's disease, acute fatty liver of pregnancy, amebic abscesses, and disseminated tuberculosis.

Acute liver failure encompasses both fulminant hepatic failure (FHF) and sub-fulminant hepatic failure (or late-onset hepatic failure). FHF is generally used to describe the development of encephalopathy within 8 weeks of the onset of symptoms in a patient with a previously healthy liver. Sub-fulminant hepatic failure is reserved for patients with liver disease for up to 26 weeks prior to the development of hepatic encephalopathy.

FHF is usually defined as the severe impairment of hepatic functions in the absence of pre-existing liver disease. FHF may result from exposure of a susceptible individual to an agent capable of producing serious hepatic injury. Examples of such agents include infectious agents, excessive alcohol, hepatotoxic metabolites, and hepatotoxic compounds (e.g., drugs). Other causes include congenital abnormalities, autoimmune disease, and metabolic disease. In many cases the precise etiology of the condition is unknown (e.g., idiopathic). FHF may be diagnosed, for example, using the liver function assays described above.

By means of another example, Multiple Organ Failure is generally defined as parenchymal cell loss associated with a local and systemic inflammatory response. More specifically, organ failure is the failure of an essential system in the body requiring medical intervention. Multiple organ dysfunction syndrome (MODS) is altered organ function in an acutely ill patient requiring medical intervention to perform homeostasis. MODS usually involves two or more organs.

MODS typically results from infection, injury (accident, surgery), hypoperfusion and hypermetabolism. Following an initiating event, an uncontrolled inflammatory response ensues, which causes tissue injury and triggers local and systemic responses. Respiratory failure is common in the first 72 hours after the original insult, hepatic failure is common in the first 5-7 days, gastrointestinal bleeding may occur at 10-15 days, and renal failure is common at 11-17 days. Mortality rates for MODS vary from 30% to 100%. There is currently no effective therapeutic regimen available to reverse established MODS.

By means of example and not limitation, liver fibrosis is the excessive accumulation of extracellular matrix proteins including collagen that occurs in most types of chronic liver diseases. Advanced liver fibrosis results in cirrhosis, liver failure, and portal hypertension, and often requires liver transplantation. A key event in the etiology of liver fibrosis is inappropriate or excessive hepatic stellate cell activation.

The term "liver disease" applies to many diseases and disorders that cause the liver to function improperly or to cease functioning, and this loss of liver function is indicative of liver disease.

Thus, assays of liver function are frequently used to diagnose liver disease. Examples of such assays include, but are not limited to, the following:

(1) Assays to determine the levels of serum enzymes such as lactate dehydrogenase (LDH), alkaline phosphatase (ALP), aspartate aminotransferase (AST), and alanine aminotransferase (ALT), where an increase in enzyme levels indicates liver disease. One of skill in the art will reasonably understand that these enzyme assays indicate only that the liver has been damaged. They do not assess the liver's ability to function. Other tests can be used to assay a liver's ability to function.

(2) Assays to determine serum bilirubin levels. Serum bilirubin levels are reported as total bilirubin and direct bilirubin. Normal values of total serum bilirubin are 0.1-1.0 mg/dL (e.g., about 2-18 mmol/L). Normal values of direct bilirubin are 0.0-0.2 mg/dL (0-4 mmol/L). Increases in serum bilirubin are indicative of liver disease.

(3) Assays to determine serum protein levels, for example, albumin and the globulins (e.g., alpha, beta, gamma). Normal values for total serum proteins are 6.0-8.0 g/dl (60-80 g/L). A decrease in serum albumin is indicative of liver disease. An increase in globulin is indicative of liver disease.

Other tests include prothrombin time, international normalized ratio, activated clotting time (ACT), partial thromboplastin time (PTT), prothrombin consumption time (PCT), fibrinogen, coagulation factors; alpha-fetoprotein, and alpha-fetoprotein-L3 (percent).

In another aspect ADHLSC-CM or an ADHLSC-CM Fraction, or the pharmaceutical formulation comprising them, or combinations thereof, may be for use in the treatment of a proliferative disease.

The term "proliferative disease or disorder" generally refers to any disease or disorder characterized neoplastic cell growth and proliferation, whether benign, pre-malignant, or malignant The term proliferative disease generally includes all transformed cells and tissues and all cancerous cells and tissues. Proliferative diseases or disorders include, but are not limited to abnormal cell growth, benign tumours, pre-malignant or precancerous lesions, malignant tumours, and cancer.

Examples of proliferative diseases and/or disorders are benign, pre-malignant, and malignant neoplasms located in any tissue or organ, such as in the prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, or urogenital tract. An organ that may be preferably affected is the liver.

Further subject matter covered by the aspects of the invention includes any one or a combination of two or more of ADHLSC (or other suitable type of cell such as primary hepatocytes or a suitable stem or progenitor cells of liver or other origin), ADHLSC-CM or an ADHLSC-CM Fraction, or other suitable (combination of) product(s) as disclosed herein, or the pharmaceutical formulation as disclosed herein, for use in inhibiting fibrogenesis and fibrosis in vivo.

Inhibition of fibrogenesis and fibrosis in vivo may be advantageously employed in the treatment of fibrotic diseases, which are commonly typified by excessive accumulation of fibrous tissue to the detriment of parenchymal cells, and therefore by reduced function due to the loss of parenchymal cells.

Also provided is use of any one or a combination of two or more of ADHLSC, ADHLSC-CM, an ADHLSC-CM Fraction, or other suitable (combination of) product(s) as disclosed herein, or the pharmaceutical formulation as disclosed herein, for inhibiting fibrogenesis in vitro. Also provided are corresponding methods of inhibiting fibrogenesis in vitro.

Such combination of biological products can be tested in a culture system making use of HSC; using ADHLSC-based co-culture systems like the one described in the Examples as a reference, e.g., the co-culture in a Transwell® system, wherein the cells are separated by a semipermeable membrane that prevents the exchanges of cells, but allows most extracellular components to pass.

As set forth in the experimental section, the inventors demonstrated that in a co-culture system where ADHLSC were separated from HSC by a 0.4 µm pore PTFE membrane insert, ADHLSC exerted desirable effects on HSC. This illustrates at least how such combination products can be compared to the secretion products of ADHLSC that exert an effect on HSC, by passing through a filter having pore size of 0.4 µm, in particular obtaining an ADHLSC-CM fraction containing microvesicles that are smaller than 0.4 µm.

The terms "hepatic stellate cells" or "HSC" are well-understood in the field. By means of further guidance, these terms denote non-parenchymal liver cells which reside in the space of Disse within the hepatic microcirculatory unit, and can be distinguished using intravital fluorescent microscopy (IVFM) due to the autofluorescence from their intracellular vitamin A.

Also provided is a pharmaceutical formulation comprising HSC and any one or a combination of two or more of ADHLSC, ADHLSC-CM or the cell-free compositions that are obtained by fractioning ADHLSC-CM, or other suitable product(s) as disclosed herein. The pharmaceutical formulation may further comprise hepatocytes, e.g., primary hepatocytes or hepatocytes differentiated in vitro from a suitable progenitor cells, e.g., MSC or ADHLSC.

Further provided is a pharmaceutical formulation comprising hepatocytes and any one or a combination of two or more of ADHLSC, ADHLSC-CM or the cell-free compositions that are obtained by fractioning ADHLSC-CM, or other suitable product(s) as disclosed herein.

These pharmaceutical formulations may be suitably formulated as described in detail above. Composition of pharmaceutical formulation comprising live cells may impose certain requirements, such as for example, the compositions may comprise a suitable buffer system (e.g., phosphate or carbonate buffer system) to achieve desirable pH, more usually near neutral pH, and may comprise sufficient salt to ensure isoosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the compositions may comprise a carrier protein, e.g., albumin, which may increase the viability of the cells. Such requirements are well appreciated by the skilled person Where pharmaceutical formulations as formulated throughout this specification comprise cells, such as without limitation hepatocytes or ADHLSC, or other stem or progenitor cells of liver (or other) origin, the cells may be administered to human subjects without limitation in doses ranging from about $1\times10^5$ to $1\times10^{12}$ cells, such as preferably doses of about 1×10⁶ to 1×10¹⁰ cells, or doses of about 1×10⁷ to about 1×10⁹ cells, e.g., about 1×10⁷, about 1×10⁸, or about 1×10⁹ cells. However, the precise determination of a therapeutically effective dose may be based on factors individual to each patient, including their size, age, size tissue damage, and amount of time since the damage occurred, and can be readily ascertained by those skilled in the art from this disclosure and the knowledge in the art.

Such pharmaceutical formulations may be particularly useful for the treatment of diseases discussed elsewhere in this specification, more particularly liver diseases. More particularly, pharmaceutical formulations comprising cells may be intended for transplantation into the liver.

Additionally, ADHLSC-CM can be used methods for identifying a biologically active compound for the treatment of a liver disease, the method comprising;
(a) obtaining one or more fractions of a ADHLSC-CM:
(b) assaying the ability of one or more of the fractions to increase or decrease one or more biological activities (such as metabolism, proliferation, survival, activation, apoptosis, migration, engraftment, or differentiation) of one or more cells found in liver (such as hepatocytes, hepatic stellate cells, liver myofibroblasts, or hepatic sinusoidal cells) in vivo, in vitro, and/or ex vivo;
(c) selecting a fraction of the ADHLSC-CM that increase or decrease one or such activities; and
(d) identifying one or more molecules present in the selected fraction.

The ensuing clauses provide additional illustration of certain aspects and embodiments that have been disclosed in accordance with the present disclosure:

1. A cell-free conditioned medium obtainable by culturing adult-derived human liver stem/progenitor cells (ADHLSC) in a cell culture medium and separating the cell culture medium from the cells.
2. The cell-free conditioned medium according to clause 1, wherein the medium is serum-free.
3. A cell-free composition obtainable by fractioning the cell-free conditioned medium according to clause 1 or 2.
4. The cell-free composition according to clause 3, wherein said fractioning comprises filtering, enzymatically digesting, centrifuging, adsorbing, and/or separating by chromatography the cell-free conditioned medium.
5. The cell-free conditioned medium according to clause 1 or 2, or the cell-free composition according to clause 3 or 4, that contains soluble proteins and/or microvesicles.
6. The cell-free conditioned medium according to any one of clauses 1, 2 or 5, or the cell-free composition according to any one of clauses 3 to 5, comprising:
    (a) at least one of soluble proteins selected from the group consisting of: hepatocyte growth factor (HGF), Vascular endothelial growth factor (VEGF), eotaxin (CCL11), interleukin-6 (IL-6), and interleukin-8 (IL-8); and, optionally
    (b) at least one of soluble proteins selected from the group consisting of matrix metalloproteases, growth factors, chemokines, and cytokines.
7. The cell-free conditioned medium according to clauses 5 or 6, or the cell-free composition according to clauses 3 to 6, wherein the soluble proteins are present at a concentration of at least 1 ng/ml.
8. The cell-free conditioned medium according to any one of clauses 1, 2 or 5 to 7, or the cell-free composition according to any one of clauses 3 to 7, wherein said microvesicles are selected according their size, molecular weight, and/or composition.
9. The cell-free conditioned medium according to any one of clauses 1, 2, or 5 to 8, or the cell-free composition according to any one of clauses 3 to 8 that is concentrated at least about 5-fold, at least about 10-fold, at least about 20-fold, at least about 50-fold, or at least about 100-fold.
10. The cell-free conditioned medium according to any one of clauses 1, 2, or 5 to 8, or the cell-free composition according to any one of clauses 3 to 8 that is diluted at least about 5-fold, at least about 10-fold, at least about 20-fold, at least about 50-fold, or at least about 100-fold.
11. A method for producing a cell-free conditioned medium comprising the steps of culturing ADHLSC in a cell culture medium and separating the cell culture medium from ADHLSC.
12. The method for producing a cell-free conditioned medium according to clause 11, wherein:
    (a) the cell culture medium is a serum-free medium; and/or
    (b) the cell culture medium is separated from ADHLSC after culturing ADHLSC in the cell culture medium for at least 2 hours, at least 4 hours, at least 6 hours, at least 8 hours, at least 12 hours, or at least 24 hours.
13. The cell-free conditioned medium of any one of clauses 1, 2, or 5 to 10 or the cell-free composition of any of clauses 3 to 10, for use as a medicament.
14. The cell-free conditioned medium of any one of clauses 1, 2, or 5 to 10 or the cell-free composition of any of clauses 3 to 10, for use as a medicament in combination with one or more exogenous active ingredients.
15. A pharmaceutical formulation comprising a pharmaceutically effective amount of any one of the cell-free conditioned medium of any one of clauses 1, 2, or 5 to 10 or the cell-free composition of any of clauses 3 to 10.
16. A pharmaceutical formulation comprising a pharmaceutically effective amount of a combination of any one of the cell-free conditioned medium of any one of clauses 1, 2, or 5 to 10 and/or the cell-free composition of any of clauses 3 to 10, and one or more exogenous active ingredients.
17. The cell-free conditioned medium of any one of clauses 1, 2, or 5 to 10, the cell-free composition of any one of clauses 3 to 10, or the pharmaceutical formulation according to any one of clauses 15 or 16, or a combination of two or more thereof, for use in the treatment of a fibrotic disorder.
18. The cell-free conditioned medium of any one of clauses 1, 2, or 5 to 10, the cell-free composition of any one of clauses 3 to 10, or the pharmaceutical formulation according to any one of clauses 15 or 16, or a combination of two or more thereof, for use in the treatment of a liver disorder.
19. The cell-free conditioned medium of any one of clauses 1, 2, or 5 to 10, the cell-free composition of any one of clauses 3 to 10, or the pharmaceutical formulation according to any one of clauses 15 or 16, or a combination of two or more thereof, for use in the treatment of organ injury or failure.
20. The cell-free conditioned medium of any one of clauses 1, 2, or 5 to 10, the cell-free composition of any one of clauses 3 to 10, or the pharmaceutical formulation according to any one of clauses 15 or 16, or a combination of two or more thereof, for use in organ or cell transplantation.

21. A method of treating a disorder in a subject in need of said treatment comprising the administration of a therapeutically or prophylactically effective amount of the cell-free conditioned medium of any one of clauses 1, 2, 5 to 10, the cell-free composition of any one of clauses 3 to 10, or the pharmaceutical formulation of clause 15 or 16, or of a combination of two or more thereof, to the subject.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as follows in the spirit and broad scope of the appended claims.

The herein disclosed aspects and embodiments of the invention are further supported by the following non-limiting examples.

EXAMPLES

Example 1—Profile of ADHLSC and HSC Secretome as Established in Conditioned Media Materials & Methods
ADHLSC and HSC Isolation and Culture The protocol and experiments were approved by the ethical committees of the St-Luc Hospital and faculty of Medicine of Université catholique de Louvain. An agreement from the Belgian Ministry of Health was obtained for the Hepatocytes and Hepatic Stem Cells Bank. A written and signed informed consent has been obtained for each human liver used in the current study. Four donors were used in the current study, as shown in Table 1.

TABLE 1

| Donor number (Age) | Gender | Reason of death | Blood group | Ischemia time |
|---|---|---|---|---|
| 89 (3 days) | M | Respiratory | A+ | 4 hours |
| 93 (2 years) | F | Metabolic disease (liver transplanted) | O+ | 1 hour 43 min |
| 97 (7 months) | F | Meningitis | A+ | 5 hours 30 min |
| 98 (7 days) | M | Cardio-respiratory arrest | O− | 4 hours 20 min |

ADHLSC were obtained subsequently to primary culture of the liver parenchymal fraction previously obtained after a two-step collagenase perfusion, filtration and low speed centrifugation, as previously described (Najimi M et al., 2007; WO2007/071339). HSC were isolated from the corresponding non-parenchymal fraction using a Nycodenz® gradient centrifugation step (Myegaard, Oslo, Norway) as previously described (Guimaraes E et al. 2010).

Both cell types were cultured using DMEM containing 4.5 g/L glucose (Invitrogen) supplemented with 10% v/v Fetal Calf Serum (PAA) and 1% Penicillin/Streptomycin (Invitrogen), at 37° C. in a fully humidified atmosphere (5% CO2). When reaching 80% confluence, cells were lifted with 0.05% trypsin-EDTA (Invitrogen) and re-plated at a density of 5000 cells/cm². The viability of recovered cells was evaluated using trypan blue exclusion assay.

Flow Cytometry

Cells were re-suspended in commercially available Dulbecco's Phosphate-Buffered Saline (D-PBS) at a concentration of 2×10⁵ cells/ml. For intracellular immunostaining, cell permeabilization was performed with cytofix/cytoperm for 20 minutes at 4° C. (BD Pharmingen). Cells were then washed and incubated for 30 minutes at 4° C. with the fluorescently labelled antibodies (see Table 2). The corresponding control isotypes were used in parallel to evaluate the non-specific binding. After washing, cells were suspended in Stabilizing Fixative (BD Pharmingen) before reading with a CANTO II flow cytometer. The analyses were performed using the BD FACSDiva Software.

TABLE 2

| Ab | F | CI | Suppl. | Ref. | Conc. |
|---|---|---|---|---|---|
| Anti-CD29 | APC | MsIgG1, k | BD | 559883 | 1/10 |
| Anti-CD44 | FITC | MsIgG2b, k | BD | 555478 | 1/10 |
| Anti-CD45 | PE-Cy7 | MsIgG1, k | BD | 557748 | 1/10 |
| Anti-CD73 | PE | MsIgG1, k | BD | 550257 | 1/10 |
| Anti-CD90 | APC | MsIgG1, k | BD | 559869 | 1/10 |
| Anti-CD117 | APC | MsIgG1, k | BD | 550412 | 1/10 |
| Anti-CD133/2 | PE | MsIgG1 | Miltenyi | 130-080-901 | 1/5 |

(Ab: antibody specificity,
F: fluorochrome,
CI: corresponding isotype,
Suppl.: commercial supplier,
Ref.: supplier's reference,
Conc.: concentration for flow cytometry analysis)

Production of Conditioned Media for ADHLSC and HSC (ADHLSC-CM and HSC-CM)

When 60-70% of confluence was reached, the cells were washed and the conditioned medium was replaced by fresh medium without 10% v/v Fetal Calf Serum. After 24 hours incubation, supernatants were collected and stored for further assays. Corresponding cells were lifted for counting and viability evaluation. The concentration of secreted protein is expressed as nanograms (ng) or picograms (pg) that are secreted in 24 hours by 10⁵ cells during 24 hours.

ELISA

The ELISA analyses were performed on culture supernatants collected 24 hours after incubation with serum-free medium. The growth factors and cytokines concentrations were calculated for 10⁵ cells. The measurement of the absorbance at 450 nm was done with a Victor X4 plate Reader (PerkinElmer).

Collagen secretion analysis was performed by using an ELISA kit for the procollagen type I C-Peptide (Takara Bio Inc, Japan). Hepatocyte Growth Factor (HGF) and Transforming Growth Factor beta 1 (TGFβ1) levels in the culture supernatants were assayed by using Quantikine ELISA Kits from R&D Systems. For HGF and TGFβ1 kits, a reading at 570 nm was subtracted to the 450 nm reading to correct the optical imperfections of the plates. The experiments were performed according to the manufacturer's instructions. For TGFβ1 ELISA, samples were activated by acidification followed by neutralization in order to make latent TGFβ1 detectable by using the Quantikine TGFβ1 immunoassay.

Luminex Analysis

The Bio-Plex Pro Human Cytokine 27-plex Assay kit (including IL-1b, IP-10, IL-2, IL-4, IL-6, IL-7, IL-188 9, IL-10, IL-13, IL-15, Eotaxin, FGF, GM-CSF, interferon-gamma (IFN-γ), MIP-1a, MIP-1b, RANTES, TNFα, IL-1ra, IL-5, IL-8, IL-12, IL-17, G-CSF, MCP-1, PDGF-bb and VEGF; Bio-Rad) and the Luminex technology (Bio-Plex 200, Biorad) was used to investigate the secretome of both liver cell types. The principle of the technique is based on color-coded beads and enables to detect up to 100 cytokines simultaneously. The primary antibody directed against the target protein is conjugated with the dyed beads. After several washes to remove unbound proteins, a secondary biotinylated antibody is added to the reaction. Streptavidin-phycoerythrin (Streptavidin-PE) is then added to bind the biotinylated antibody. By measuring the relative fluorescence intensity, the antigen-antibody reaction can be measured.

The assays were performed following the manufacturer's instructions. Briefly, after the pre-wetting of the plate, 50 µl of the beads were added in each well and washed twice. 50 g of the samples (serum free culture supernatants recovered after 24 hours of culture) were added to the plate. The plate was shaken during 30 seconds and then incubated for 45 minutes on a plate shaker at 120 rpm at room temperature. The plate was washed three times with the Bio-Plex wash buffer and 251 of the detection antibody was added in each well and incubated for 30 minutes on a plate shaker at 120 rpm. The plate was then washed three times with the Bio-Plex wash buffer and 50 g of the Streptavidin-PE solution was added in each well. The plate was shaken during 30 seconds and incubated for 10 minutes on a plate shaker at 120 rpm. Finally, after three washes of the plate with the Bio-Plex wash buffer, the beads were re-suspended with 125 µl of Bio-Plex Assay Buffer. The plate was read by the Luminex machine and the data were analyzed using Bio-Plex Manager 6.0.

Statistics

Results are expressed as mean standard error of the mean (SEM). Statistical differences were determined by Student's t test for two groups' comparison. The statistical significance of the differences between samples or conditions was established with the p values $*p<0.05$, $p<0.01$, and $*p<0.001$.

Results

ADHLSC and HSC were isolated in four independent liver donors. For each of them, HSC and ADHLSC were obtained in parallel and then cultivated under the same culture conditions and concomitantly followed. The fibroblastic morphology displayed by both cell types remained stable over the different studied passages and the population cumulative doubling was similar for the two cell types. The mesenchymal phenotype of both cell types was investigated by exploring the expression of several specific appropriate markers using flow cytometry. Both cell types were immuno-positive for most of the membrane markers widely used to characterize mesenchymal stem cells. This was the case for mesenchymal stem cells markers (such as CD73 and CD90) and extracellular matrix markers (such as CD29 and CD44) for which expression levels were not significantly different between ADHLSC and HSC for the analysed passages. The mesenchymal phenotype of both cell types was also supported by the negative expression of hematopoietic markers like CD45, CD117 and CD133 as demonstrated using flow cytometry. This data thus confirmed the presence of mesenchymal markers in both ADHLSC and HSC as reported before (Kordes C et al., 2007; Kordes C et al., 2013; Najimi M et al., 2007).

The secretome of ADHLSC and HSC across the four donors was partially analysed by using the conditioned medium of cell cultures in protein-specific immunoassays. The experiments were performed on supernatants collected 24 hours after incubation with serum free medium, obtaining a conditioned media that is called ADHLSC-CM and HSC-CM, respectively.

The analysis started by detecting proteins known to be expressed by activated HSC. No significant difference was observed between HSC-CM and ADHLSC-CM in the concentration of secreted procollagen type-I C-Peptide (about 130 ng/ml/$10^5$ cells/24 hours) and TGFβ1, one of the most powerful pro-fibrotic cytokines and involved in inflammatory and immune responses (about 90 ng/ml/$10^5$ cells/24 hours). A significant difference between HSC-CM and ADHLSC-CM is observed in the secretion of hepatocyte growth factor (HGF), a hepatocyte mitogen with anti-inflammatory properties and having crucial physiological functions including organ protection and regeneration. Following liver injury, HGF is known to be secreted by distant organs such as spleen, lungs and kidneys as well as by sinusoidal cells such as Kupffer cells and HSC. ADHLSC-CM contains about three times more HGF than HSC (FIG. 1A).

Figure 1B:
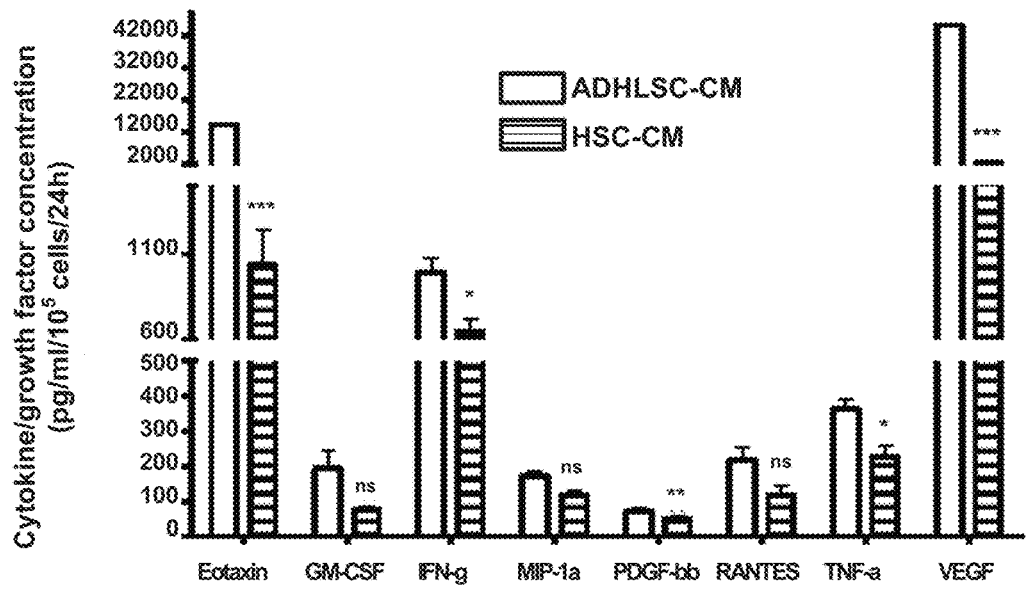
Figure 1C:
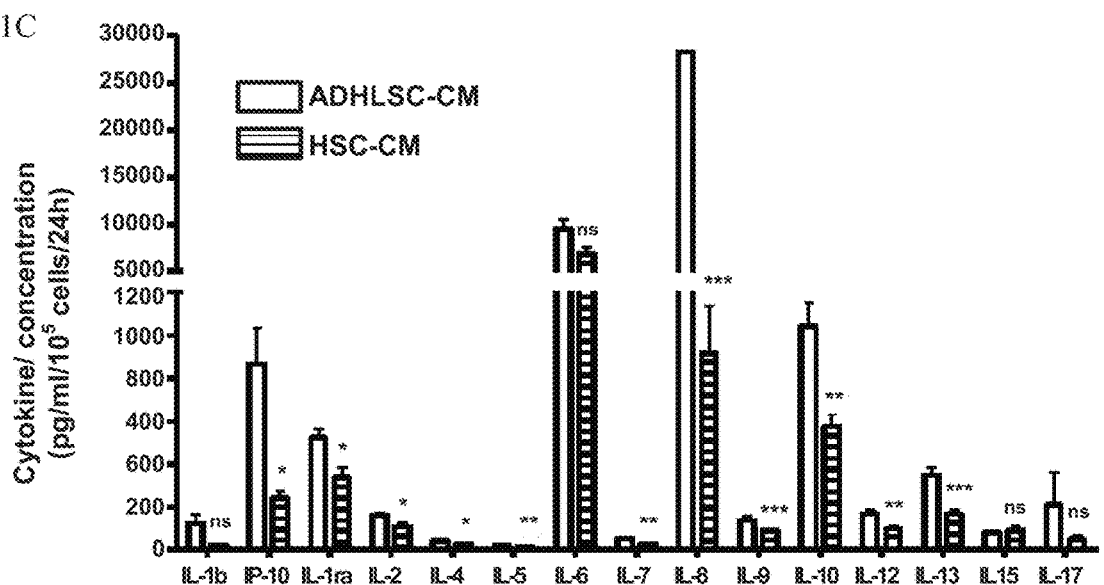

The secretion of a larger panel of major growth factors, chemokines and cytokines was performed using a multiplex technology. ADHLSC clearly appear secreting statistically significant higher levels of VEGF, IFN-g, Eotaxin (CXCL11), IL-8 and IL-10 when compared to HSC, with concentration superior to 1 ng/ml/$10^5$/24 hours in ADHLSC-CM. At lower absolute levels (i.e., equal to or below 1 ng/ml/$10^5$/24 hours), PDGF-bb, TNF-α, IP-10, IL-5, IL-7, IL-9, IL-12, and IL-13 are also present at higher concentration in ADHLSC-CM (FIGS. 1B and 1C). The statistically significant increased concentration of specific cytokines and growth factors in ADHLSC-CM can be vary from about 2 times (as for IL-5, IL10 and IL-13) up to 10 or even 30 times (as Eotaxin, VEGF, and IL-8) more than HSC-CM. Other cytokines were either undetectable in both cell types (such as bFGF) being more variable across donors (data not shown).

If such data are compared with those previously determined for the conditioned media obtained from a different liver pluripotent progenitor (HLSC-CM; as described in WO2009/150199) or bone marrow Mesenchymal Stem cells (MSC-CM; as described in WO2009/150199), it is also evident that the composition of ADHLSC-CM is qualitatively different also from these conditioned media, as shown in Table 3.

TABLE 3

| Protein | HLSC-CM (selected from Table 1 of WO2009/150199; expressed as pg/ml/$10^6$ cells/24 hours) | MSC-CM | ADHLSC-CM (selected from FIG. 1; expressed as pg/ml/$10^5$cells/24 hours) |
|---|---|---|---|
| Eotaxin | 5.1 | 3.96 | ≥14335.6 |
| IFN-gamma | 38.46 | 104.73 | 990 ± 91.8 |
| VEGF | 896.9 | 4961.43 | ≥45306.2 |
| TNF-alpha | 3.7 | 13.04 | 362.1 ± 33.3 |
| IL8 | 4205.64 | 51.04 | ≥28231.7 |

TABLE 3-continued

| Protein | HLSC-CM (selected from Table 1 of WO2009/150199; expressed as pg/ml/$10^6$ cells/24 hours) | MSC-CM | ADHLSC-CM (selected from FIG. 1; expressed as pg/ml/ $10^5$cells/24 hours) |
|---|---|---|---|
| IP-10 | 0.0 | 0.0 | 867.2 ± 184.2 |
| HGF | 5719 | 2.3 | 936.6 ± 151.9 |
| IL2 | 0.0 | 0.0 | 160.1 ± 14.7 |

Even if the proteins cited in Table 3 represent only some of the most representative examples, the differences between the published data and those obtained using ADHLSC-CM are also remarkable taking in consideration the fact that concentration for HLSC-CM and MSC-CM are indicated in WO2009/150199 for 10 times more cells. It is evident that ADHLSC secretome is particularly enriched with a combination of useful secreted proteins, such as growth factors, chemokines, and cytokines that are present in different ratio and amount than in other known conditioned media.

Thus, ADHLSC secretome, in general and in particular when specifically obtained and characterized as ADHLSC-CM, represents a feature distinguishing ADHLSC not only from HSC but also from other liver or mesenchymal cells and their secretome. These molecular features may have substantially distinctive effect on how not only ADHLSC themselves proliferate, are biologically active, and interact with other cells in vivo and in vitro, but also on how ADHLSC may affect biological activities exerted by other cells types within the organism, and in particular within liver. Indeed, potential beneficial effects of medical interest may be provided by ADHLSC-CM, as such or a given fraction thereof, alone, in combination or not with ADHLSC or any other appropriate cell-based, protein-based, and/or chemical drug-based treatment.

Example 2—Effects of ADHLSC on HSC Proliferation and Secretion Profile

Materials & Methods
ADHLSC/HSC Co-Culture Model

The indirect co-culture system (Transwell® COL Collagen-Coated 0.4 μm Pore PTFE Membrane Insert) was used. In brief, HSC were seeded in the lower chamber at a density of 10 000 cells/cm² while ADHLSC were placed on the membrane insert, with ADHLSC/HSC ratios (cell #/cell #) of 0/1 (control) and 1/100. HSC were collected and analysed at the indicated time points.

Assays for Comparing ADHLSC and ADHLSC-CM Effects on HSC

ADHLSC-CM and HSC-CM was obtained as indicated above, by collecting ADHLSC and HSC supernatants, respectively, after 24 hours of culture in absence of serum. HSC were incubated with ADHLSC (using two co-culture system), HSC-CM, or ADHLSC-CM for 24 hours. The experiments were performed by using ADHLSC, ADHLSC-CM, HSC, and HSC-CM from the same donor (autologous conditions) but repeated also by combining cells or conditioned media from different donors, obtaining qualitatively similar results.

CCK-8 biochemical assay was performed by using the Cell Counting Kit—8 BioChemika (Fluka; cat. No. 96992). Propidium iodide assay was performed according to general literature.

For cell cycle analysis, HSC were lifted with 0.05% trypsin-EDTA (Invitrogen) After 24 hours of co-culture.

After centrifugation, cells were washed twice with PBS and fixed with 700 μl of cold ethanol and incubated for 30 minutes on ice. The cells were washed again with PBS before being incubated with a solution containing 100 μg/ml Propidium Iodide (PI, Invitrogen), 0.1 mg/ml RNase (Sigma) and 0.01% Triton X-100 (Sigma) for 30 minutes at 37° C. and then for 15 minutes on ice, before reading with a CANTO II flow cytometer. The analyses were performed using the BD FACSDiva Software. The different phases of the cell cycle were determined by measuring the area under curve with the FlowJo Software.

For Ki-67 immunocytochemistry, HSC were incubated 24 hours with the conditioned media and then fixed using paraformaldehyde 3.5%, for 15 min at room temperature. Endogenous peroxidase was eliminated using hydrogen peroxide 3.3% for 3 minutes. All steps were performed at room temperature. Cells were permeabilized using PBS containing 1% Triton X-100 (Sigma) for 10 minutes. Non-specific immuno-staining was prevented by 1 h incubation in PBS containing 1% Bovine Serum Albumin (Sigma). Thereafter, cells were incubated with Ki67 antibody (Dako) for 1 h. After washing, cells were incubated with secondary antibody (EnVision-Dako) during 30 minutes. Detection was performed after 5 minutes incubation with liquid DAB and substrate chromogen (Dako). Counterstaining was performed using Mayer's hematoxylin for 10 minutes. Preparations were then mounted for microscopic analysis (DMIL, Leica, Belgium). For each condition, four different fields were analyzed and a total of 2500 stained/unstained nuclei were counted using the ImageJ Software.

Results

Fibrogenesis by activated HSC largely contributes to processes resulting in fibrosis of the liver tissues. HSC are "activated" in vivo during liver injury, and evolve to myofibroblast-like cells, with consequent increase in cell proliferation and extracellular matrix protein deposition. At the structural level, activated HSC lose their big vitamin A-containing lipid droplets and up-regulate the expression of some cell adhesion molecules, as well as the secretion of pro-inflammatory cytokines. In vitro, the fibrotic part of this activation process is mimicked by culturing HSC on plastic culture dishes. The effect of ADHLSC in general (and of ADHLSC-CM in particular) on HSC activation and fibrogenesis can be studied in vitro by making use of indirect co-culture systems wherein HSC and ADHLSC are cultured in two cell culture chambers communicating only through a membrane having a specific composition, surface, and pore size.

Figure 2A:
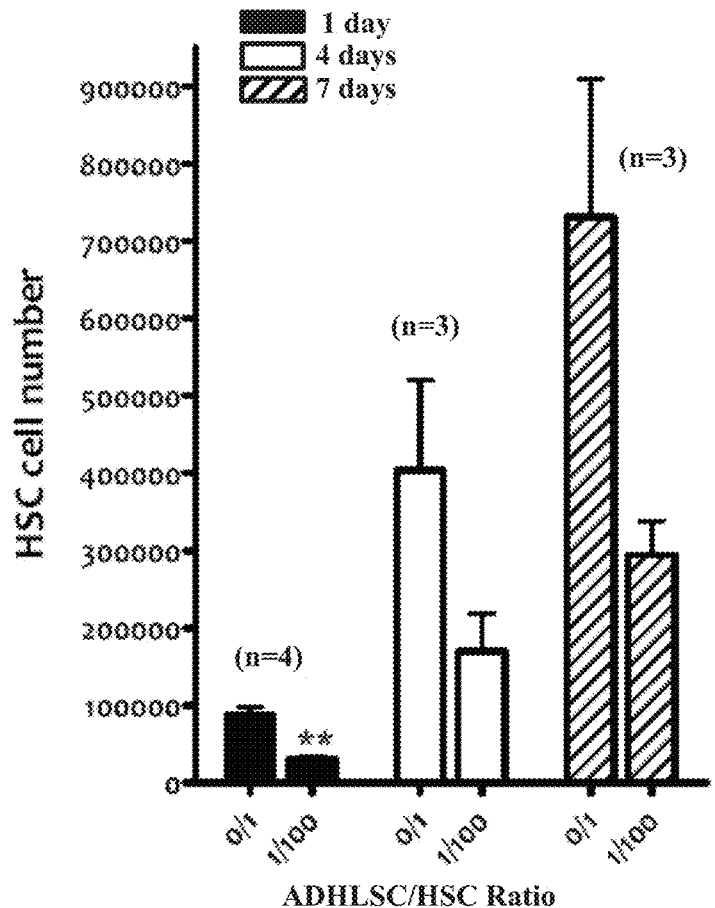
FIGS. 2A-2B: effect of ADHLSC on HSC number and viability in the Transwell® co-culture system. The effect of exposing HSC to ADHLSC is determined by comparing HSC number when cultured in absence of ADHLSC (control, 0/1) or when cultured at low ADHLSC/HSC ratio (1/100) at distinct time points (FIG. 2A), and then using CCK-8 biochemical assay for determining post-seeding HSC number (FIG. 2B). For the analysis of statistically relevant differences between the two conditions, ** denotes a p value <0.01. n: number of donors for which the experiment was performed.

Since activated HSC are characterized by an increased proliferation rate, the first analyses concerned the proliferation of HSC after co-culture with ADHLSC. The cell number analysis was performed using manual counting after the HSC were collected 24 hours, 4 days and 7 days post-seeding. Using cells from 4 different donors, a significant decrease in the number of HSC was noted. In this experiment, a statistically relevant decrease of the number of HSC was obtained already by using a ratio between ADHLSC and HSC of 1/100 and comparing with HSC cultured in absence of ADHLSC (FIG. 2A). This inhibitory effect at such a low ratio appears initiated in the first 24 hours, because no change in the index proliferation rate was noticed between all groups of cells.

Figure 2B:
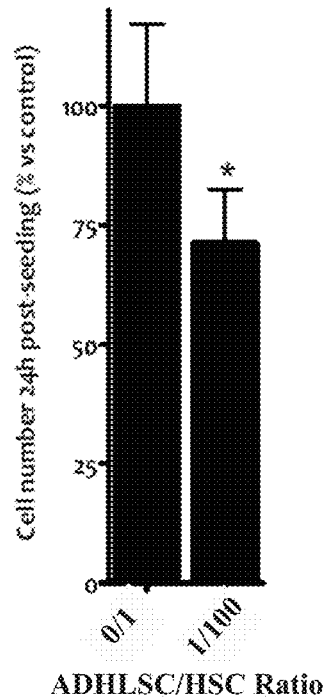

This effect was confirmed using the same ratio between ADHLSC and HSC and a CCK-8 biochemical assay, a sensitive calorimetric assay that allows the determination of the number of viable cells in cell proliferation assays (FIG. 2B).

Figure 3A:
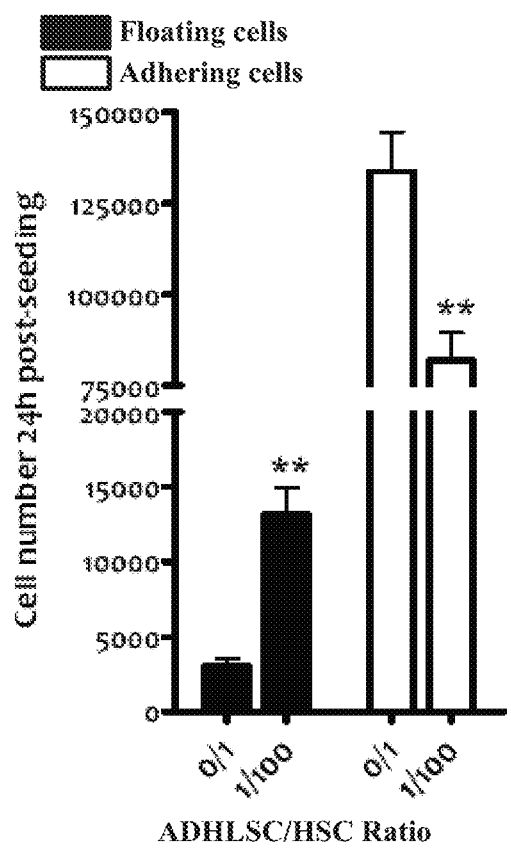
FIGS. 3A-3B: effect of ADHLSC on HSC proliferation and adherence. The assay is based on the determination of floating or adherent HSC in the Transwell® co-culture system after culturing HSC for 24 hours in presence of ADHLSC that secrete biological molecules passing across the collagen-treated membrane separating the two chambers and having a pore size of 0.4 μm (FIG. 3A) or by directly culturing HSC in ADHLSC-CM or HSC-CM (FIG. 3B). The effect on the number of floating or adherent HSC has been also tested at lower ADHLSC/HSC ratios (1/1000 and 1/10000), but the number of floating cells also decreased consequently, suggesting that 1/100 ratio is a particularly effective experimental condition for evaluating the effect of ADHLSC. For the analysis of statistically relevant differences between the two conditions, ** denotes a p value <0.01 and* denotes a p value <0.05. n: number of donors for which the experiment was performed.

When the effect on adherent and floating HSC is evaluated, it evident that a low ratio ADHLSC/HSC of 1/100 provides already a statistical relevant decrease of HSC plating, since the number of floating HSC is significantly increased (FIG. 3A).

Figure 3B:
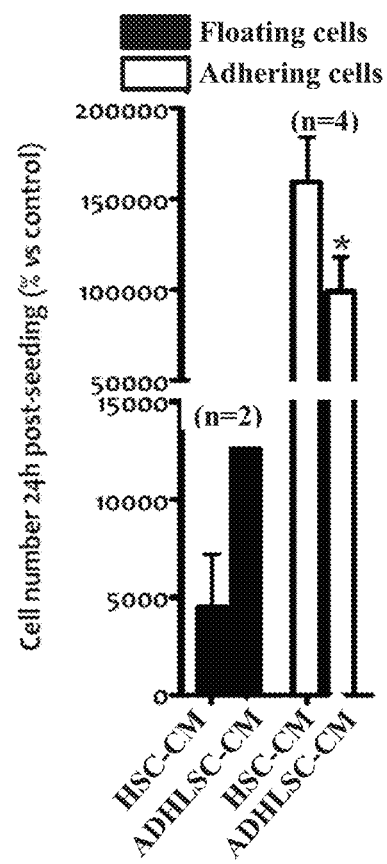

Such experiment is repeated by using only conditioned culture medium of ADHLSC (ADHLSC-CM) in order to evaluate its effect on HSC proliferation and adherence, using the conditioned culture medium of HSC (HSC-CM) as a control. The effect of ADHLSC-CM was qualitatively similar to the effect observed with ADHLSC in the co-culture system, suggesting the involvement of soluble factor(s) that are secreted by ADHLSC and pass across the membrane separating the two chambers (FIG. 3B). Using flow cytometry and Propidium Iodide staining, no significant difference in cell death induction between the HSC cultivated with ADHLSC-CM and those cultivated with HSC-CM (data not shown).

Figure 4A:
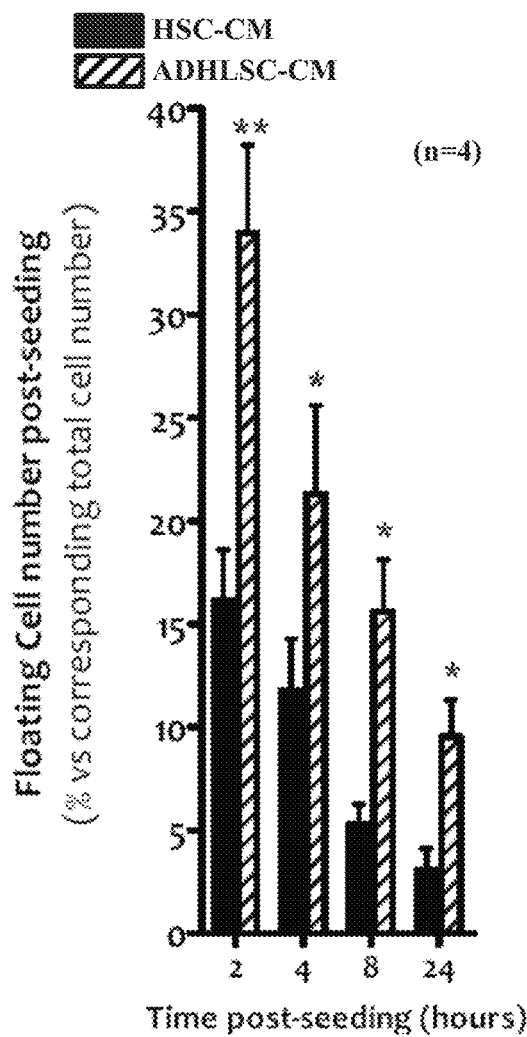
FIGS. 4A-4B: analysis of ADHLSC-CM and HSC-CM effects on HSC adherence. Post-seeding floating HSC (FIG. 4A) and adherent (FIG. 4B) HSC are determined at intermediate time points after adding ADHLSC-CM or HSC-CM. For the analysis of statistically relevant differences between the effects of ADHLSC-CM and HSC-CM, ** denotes a p value <0.01 and * denotes a p value <0.05. n: number of donors for which the experiment was performed.
Figure 4B:
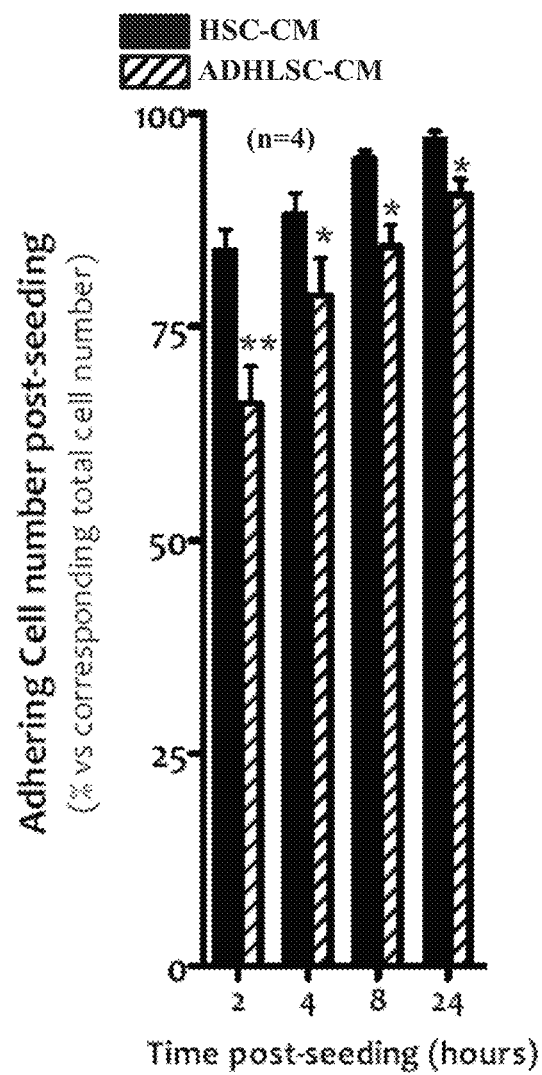

In order to investigate the mechanisms involved in the diminution of HSC number due to ADHLSC-CM, the HSC plating kinetic in presence of either ADHLSC-CM or HSC-CM was also analysed by counting the adherent and the floating cells after 2, 4, 8 and 24 hours post-seeding demonstrating a delay of the HSC plating when cultivated with the ADHLSC-CM when compared to HSC-CM that is maintained though all the time points (FIGS. 4A and 4B).

The effects of ADHLSC-CM or ADHLSC on HSC cell cycle were tested by using propidium iodide (PI) staining and flow cytometry. An increase in the number of HSC that are blocked in G0/G1 phase and a decrease of the number of HSC in the G2/M phase is clearly observed when HSC are incubated either with ADHLSC in the co-culture system (FIG. 5A) or with ADHLSC-CM (FIG. 5B). Such evidences were confirmed by Ki67 staining analysis using immunocytochemistry. A significant decrease in the number of stained HSC nuclei after an incubation of 24 hours with ADHLSC-CM in comparison with the HSC incubated with HSC-CM is observed (FIG. 5C).

Figure 6A:
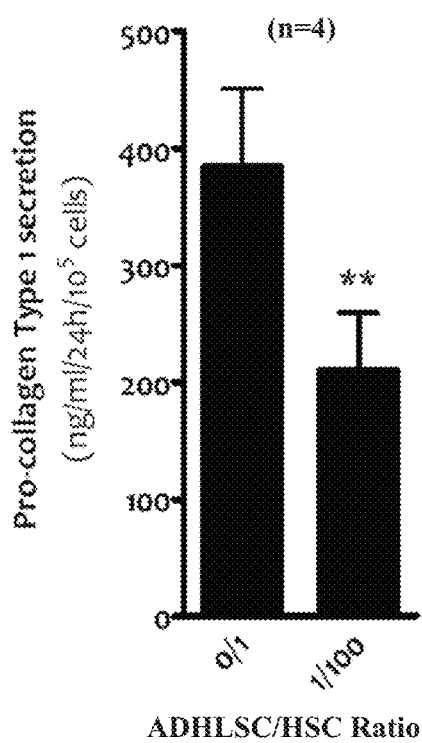
FIGS. 6A-6B: effect of ADHLSC on the HSC secretion of factors relevant to fibrogenesis in the Transwell® co-culture system, such as collagen type I (FIG. 6A) and HGF or IL-6 (FIG. 6B). After being exposed to ADHLSC for 24 hours, the medium in chamber containing HSC was substituted with serum-free medium and incubated further 24 hours before measuring the concentration of these proteins that are secreted in this serum-free medium. For the analysis of statistically relevant differences between the effects of different conditions, ** denotes a p value <0.01. n: number of donors for which the experiment was performed.
Figure 6B:
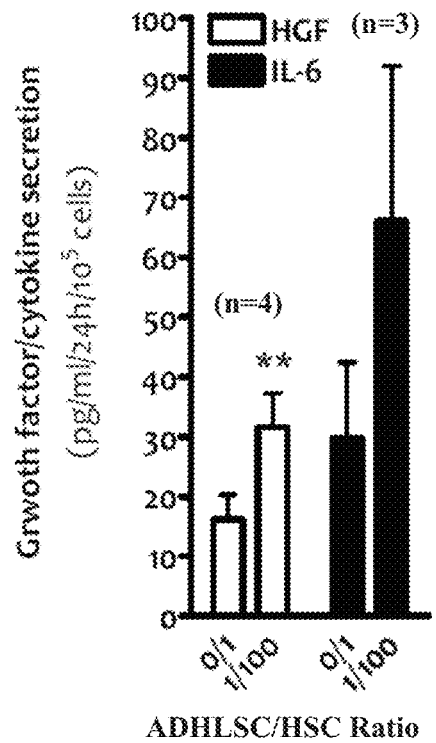

Altogether, these data demonstrate a clear decrease in the number of HSC observed after co-culture with ADHLSC or ADHLSC-CM, which could be due to an inhibition of both plating efficiency and cell proliferation of HSC. It is important to point out that this effect is obtained by combining ADHLSC and HSC from different donors, as well as by containing ADHLSC-CM directly with HSC, and not using the co-culture system. This observation suggests that a component of ADHLSC-CM that can pass across the selected membrane is actually providing this effect on HSC. Activated HSC are known to secrete collagen type I, one of the major components of the extracellular matrix. Therefore, influence of ADHLSC on the collagen secretion capacity of HSC by measuring the pro-collagen I (precursor of the collagen type I) secretion was tested using an ELISA assay. The HSC were incubated during 24 hours with ADHLSC or with ADHLSC-CM. The culture medium was changed after 24 hours and replaced by a serum-free medium. The supernatants were collected after 24 hours and the HSC were lifted for counting and viability evaluation. A significant decrease in the amount of pro-collagen I secreted by HSC after co-culture with ADHLSC at an ADHLSC/HSC ratio of 1/100 in comparison with the control group was observed (FIG. 6A). Moreover, by using a multiplex Luminex assay, it can be demonstrated that the secretion of HGF, a growth factor known to have anti-fibrotic properties, and IL-6 is increased in the culture supernatants of HSC that were previously incubated during 24 hours with ADHLSC using the co-culture system (FIG. 6B; similar data were obtained using ADHLSC-CM). At the same time, the secreted levels of metalloproteinases MMP1 and MMP2, enzymes are involved in the extracellular matrix degradation are also increased in all tested donor by at least 1.5 fold (as determined by using the multiplex technology described above). The combination of all these up- and down-regulation of proteins involved in fibrogenesis suggests that ADHLSC-CM (and in particular the component that can pass through the membrane used in the co-culture system) has a global anti-fibrotic effect on HSC that can be exploited for therapeutic applications, such as for treating liver fibrotic disorders.

The data above support that ADHLSC-CM (and specific components defined according to the method of preparation, the molecular weight or other relevant features) can be used as a component in a pharmaceutical composition, or within a method of treatment, where it can be used for providing a biologically balanced mixture of useful cell secretion products, such as growth factors, cytokines, chemokines, and other mediators of physiological activities. ADHLSC-CM can be obtained by ADHLSC applying an approach similar to one described in Example 1 as a cell-free composition and then further purified and/or concentrated (e.g. by filtration, fractionation, chromatography, enzymatic digestion, centrifugation, absorption, or any combination of them), at the scope of obtaining ADHLSC-CM preparations that are enriched in all, most, or some of its specific components, including soluble proteins and/or vesicular structures (e.g. microvesicles having a diameter of below 1 μm (such as particularly below 1.0 μm), below 0.4 μm, below 0.1 μm, or comprised between 1 μm (such as particularly 1.0 μm) and 0.1 μm, or between 0.4 μm and 0.1 μm), that are released by ADHLSC.

Example 3—In Vivo Models and Pharmaceutical Uses of ADHLSC-CM and Derived Cell-Free Compositions ADHLSC-CM, cell-free compositions that are derived from ADHLSC-CM, and any other composition that is obtained by fractionating and, if needed, concentrated (or diluted) such compositions may be used in a series of models that are preferably selected on the basis of the known biological activities of progenitor cells that are isolated from adult liver (i.e. ADHLSC), and thus more preferably related to models of human liver diseases that may be treated by making use of such preparations.

The animals (e.g. rats, rabbits, mice) are selected and eventually treated to establish the desired model and then injected intraperitoneally, intravenously (jugular, femoral, portal, or tail vein), intra-arterially (into aorta via carotid or femoral artery), intrahepatically, or intrasplenically with a given volume (e.g., 0.01-1 ml) of ADHLSC-CM, or an equivalent amount of the protein fraction of ADHLSC-CM, or an equivalent amount of the microvesicles fraction of ADHLSC-CM. Suitable controls may include an identical cell culture medium not conditioned by any cells, or an identical medium conditioned by culturing Hepatic Stellate Cells, Mesenchymal Stem Cells (such as bone marrow MSC) or any other cell type or population, as such or as a corresponding fraction thereof, and alone or in combination with any other appropriate drug or treatment that is applied simultaneously, previously, or subsequently to the administration of ADHLSC-CM, or an equivalent amount of the protein fraction of ADHLSC-CM, or an equivalent amount of the microvesicles fraction of ADHLSC-CM (including the use of a cell-based therapy based on ADHLSC or any other cell). In this manner, any treatment or drug regimen that may act synergistically with ADHLSC-CM, or an equivalent amount of the protein fraction of ADHLSC-CM, or an equivalent amount of the microvesicles fraction of ADHLSC-CM can be determined. Remission, survival, prevention, or any other appropriate end-point or marker to be measured in vivo (or selected tissues, organs, or body fluids) for determining a therapeutic effect of the preparation that is administered to the animals is monitored throughout predetermined time periods, taking into account the results obtained with available positive or negative control treatments.

A non-exhaustive list of such models and related indications include the models that are described in the literature cited in the Background, as well as others such as the D-galactosamine/endotoxin-induced mouse model of fulminant hepatic failure (FHF), the rat sepsis model of LPS-induced multi-organ failure due to LPS injection (generally, in aged rats, LPS is injected and the caecum is perforated, resulting in bacterial peritonitis and all the manifestations of clinical multi-organ failure), the glycerol-induced mouse model of acute renal failure (for example, acute toxic tubular injury in C57Bl/6 mice is induced by intramuscular injection of 7.5 ml/kg body weight of 50% v/v glycerol solution), the ischemia/reperfusion-induced rat model of acute renal failure (for example, ischemia/reperfusion-type of ARF is induced in anesthetized rats by timed clamping of both renal pedicles, thereby interrupting the blood supply to the kidneys causing an ischemic insult resulting in acute loss of kidney function, i.e., ARF), the artery ligation-induced mouse model of ischemia (for example, mice are subjected to right distal femoral artery ligation using a method known in the art, causing ischemia in a hindlimb), the anti-Thy1-1 antibody-induced rat model of glomerulonephritis (e.g., glomerulonephritis (GN) is induced by intravenous administration at day 0 of 250 µg/100 g weight of anti-Thy1-1 antibody (Ab) into femoral vein of 6-week-old female Lewis rats), the chemically or cell-based mice models of tumor growth, the carbon tetrachloride ($CCl_4$)-induced mouse model of liver fibrosis.

By means of more detailed example, for FHF induction, lethal toxicity of lipopolysaccharide (LPS) on treating SCID (severe combined immunodeficiency) mice with D-galactosamine (2-amino-2-deoxy-D-galactose) is developed as previously described (Lehmann V et al., 1987). Amounts of LPS and D-galactosamine are optimised to obtain 100% lethality within a desired experimental time window, such as 8, 16 or 24 hours after injection. By means of more detailed example, chronic liver disease and liver fibrosis is mimicked in SCID-Beige mice by treatment with carbon tetrachloride ($CCl_4$) for at least 3-4 weeks, and potentially for as long as 20 weeks, as previously described (Perez Tamayo R, 1983). Mice can be treated several times a week, e.g., three times a week. They can be administered 0.04 cc of a 40 percent solution of $CCl_4$ in olive oil or vehicle by oral gavage. In models such as the above ones, it is observed how survival of the animals, or other suitable prophylactically or therapeutically relevant end-points or benefits, can be significantly improved by administration of ADHLSC-CM, or the protein fraction of ADHLSC-CM, or the microvesicles fraction of ADHLSC-CM when compared to vehicle alone, other types of (non)-conditioned media, and/or other relevant positive or negative controls.

On the basis of the results obtained in these models, the actually pharmaceutically effective amounts of ADHLSC-CM, or the protein fraction of ADHLSC-CM, or the microvesicles fraction of ADHLSC-CM can be appropriately formulated and administered, in particular to human subjects, by infusion or one or more injections, taking into account the total protein concentration and/or the number of cells from which the ADHLSC-CM-based preparation has been originally obtained cells is infused, and then adapting the pharmaceutical composition to the subject's weight, status, and ongoing treatments. The site of administration will depend on the condition or organ treated. Where systemic administration is adequate, the composition may be infused intravenously. Where localised administration is desired, this may be achieved by localised injection. By means of example, delivery to the liver may be performed via the portal vein. Access to the portal vein is by direct puncture under radiological and or ultrasound guidance, via a puncture needle, or via a percutaneous catheter, or via a Port-a-cath R device, or via a Broviac R device inserted surgically in any vessel draining to the portal vein, preferably the inferior mesenteric vein, or a colonic vein. The catheter can be left in place for several hours, preferably several days, preferably several weeks, or preferably several months up to two years, or preferably longer for repeating infusions whenever needed.

REFERENCES

Atoui R and Chin R, 2012. Cells Transl Med. 1: 200-5.
Baglio S et al., 2012. Front Physiol. 3:359.
Cavallari C et al., 2013. Oncogene. 32, 819-826.
Du Z et al., 2013. J Surg Res. 183: 907-15.
Eichelbaum K et al. 2012. Nat Biotechnol. 30: 984-90.
Guimaraes E et al. 2010. J Hepatol. 52: 389-397.
Keating A. 2012. Cell Stem Cell. 10: 709-16.
Khuu D et al., 2012. Cell Transplant. http://dx.doi.org/10.3727/096368912x659853.
Kordes C et al., 2007. Biochem Biophys Res Commun. 352: 410-7.
Kordes C et al., 2013. Cell Physiol Biochem. 31: 290-304.
Lavoie J and Rosu-Myles M, 2013. Biochimie. http://dx.doi.org/10.1016/j.biochi.2013.06.017.
Lehmann V et al. 1987. J Exp Med. 165: 657-63.
Li G et al., 2010. Cancer Science. 101: 2546-2553.
Mukherjee P and Mani S, 2013. Biochim Biophys Acta. 1834: 2226-32.
Najimi M et al., 2007. Cell Transplant, 16: 717-728.
Pan G et al., 2012. J Surg Res. 178: 935-48.
Parekkadan B et al. 2007. PLoS ONE. 26: e941.
Puglisi M et al. 2011. J Biomed Biotechnol. 2011; 2011: 860578.
Qiao L et al., 2008. Cell Research. 18:500-507.
Ren G et al., 2012. Stem Cells Trans Med. 1:51-58.
Ueno T et al., 2013. Kidney Int. 84(2):297-307
van Poll D et al., 2008. Hepatology, 47: 634-43.
Wang S et al., 2012. Journal of Hematology & Oncology, 5:19.
Wu X and Tao R, 2012. Hepatobiliary Pancreat Dis Int. 11: 360-71.

Xagorari A et al., 2013. Int J Clin Exp Pathol. 6: 831-840.
Xiao Y et al., 2013 in "Essentials of Mesenchymal Stem Cell Biology and Its Clinical Translation" (ed. Zhao R; Springer): 33-46.
Yagi H et al, 2009. Tissue Eng Part A. 15: 3377-88.
Zarrinpar A and Busuttil R, 2013. Nature Reviews Gastroenterology and Hepatology, 10: 434-440.

The invention claimed is:

1. A method of treating a liver fibrotic disorder in a subject in need thereof, comprising:
    administering to the subject a therapeutically or prophylactically effective amount of a cell-free conditioned medium,
    wherein the cell-free conditioned medium is produced by culturing adult-derived human liver stem/progenitor cells (ADHLSC) in a cell culture medium and separating the cell culture medium from the cells, wherein the ADHLSC are albumin-positive, vimentin-positive, alpha smooth muscle actin-positive, cytokeratin-19-negative and CD133-negative.

2. The method of claim 1, wherein the liver fibrotic disorder is associated or caused by a disease selected from the group consisting of: diabetes, metabolic syndrome, viral hepatitis, chronic persistent or active hepatitis, autoimmune hepatitis, alcoholic liver disease, fatty liver disease, nonalcoholic steatohepatitis (NASH), acute-on-chronic liver failure (ACLF), primary biliary cirrhosis, primary sclerosing cholangitis, biliary atresia, congenital liver disease, hepatocellular carcinoma, or liver fibrosis coincident with chronic or repeated alcohol ingestion, with infection, with liver transplant, or with drug induced liver injury.

3. The method of claim 2, wherein the disease is selected from the group consisting of ACLF, NASH, or biliary cirrhosis.

4. The method of claim 1, wherein:
    (a) the cell culture medium is a serum-free medium; and/or
    (b) the cell culture medium is separated from ADHLSC after culturing ADHLSC in the cell culture medium for at least 2 hours, at least 4 hours, at least 6 hours, at least 8 hours, at least 12 hours, or at least 24 hours.

5. The method of claim 1, wherein the cell-free conditioned medium comprises hepatocyte growth factor (HGF), vascular endothelial growth factor (VEGF), eotaxin (CCL11), interleukin-6 (IL-6), and interleukin-8 (IL-8) at a concentration of at least 1 ng/ml.

6. The method of claim 1, wherein the cell-free conditioned medium further comprises microvesicles.

7. The method of claim 6, wherein the microvesicles are smaller than 0.40 μm.

8. The method of claim 1, wherein the cell-free conditioned medium is concentrated at least about 5-fold, at least about 10-fold, at least about 20-fold, at least about 50-fold, or at least about 100-fold.

9. The method of claim 1, wherein the cell-free conditioned medium is diluted at least about 5-fold, at least about 10-fold, at least about 20-fold, at least about 50-fold, or at least about 100-fold.

10. The method of claim 1, wherein the cell-free conditioned medium inhibits cell proliferation of hepatic stellate cells (HSCs) by at least 5%.

11. The method of claim 1, wherein the cell-free conditioned medium inhibits plating efficiency of HSCs by at least 5%.

12. The method of claim 1, wherein the ADHLSC further express at least one marker selected from CD90, CD73, CD44, CD29, alpha-fetoprotein, alpha-1 antitrypsin, HNF-4 and MRP2 transporter.

13. A method of treating a liver fibrotic disorder in a subject in need thereof, comprising:
    administering to the subject a therapeutically or prophylactically effective amount of a fractioned cell-free composition,
    wherein the fractioned cell-free composition is produced by:
    (a) culturing adult-derived human liver stem/progenitor cells (ADHLSC) in a cell culture medium and separating the cell culture medium from the cells to produce a cell-free conditioned medium, wherein the ADHLSC are albumin-positive, vimentin-positive, alpha smooth muscle actin-positive, cytokeratin-19-negative and CD133-negative; and
    (b) fractioning the cell-free conditioned medium by filtering, centrifuging, adsorbing, and/or separating by chromatography; or enzymatically digesting the cell-free conditioned medium;
    wherein the fractioned cell-free conditioned medium comprises hepatocyte growth factor (HGF), vascular endothelial growth factor (VEGF), eotaxin (CCL11), interleukin-6 (IL-6), and interleukin-8 (IL-8) at a concentration of at least 1 ng/ml.

14. A method of treating a liver fibrotic disorder in a subject in need thereof, comprising:
    administering to the subject a therapeutically or prophylactically effective amount of a microvesicle fraction of a cell-free composition,
    wherein the microvesicle fraction of the cell-free composition is produced by:
    (a) culturing adult-derived human liver stem/progenitor cells (ADHLSC) in a cell culture medium and separating the cell culture medium from the cells to produce a cell-free conditioned medium, wherein the ADHLSC are albumin-positive, vimentin-positive, alpha smooth muscle actin-positive, cytokeratin-19-negative and CD133-negative; and
    (b) fractioning the cell-free conditioned medium by filtering, centrifuging, adsorbing, and/or separating by chromatography; or enzymatically digesting the cell-free conditioned medium; and
    obtaining a microvesicle fraction of the cell-free composition.

* * * * *